US012718958B2

(12) United States Patent
Awasthi et al.

(10) Patent No.: US 12,718,958 B2
(45) Date of Patent: Aug. 25, 2026

(54) APPARATUS AND METHOD FOR DETECTING HYPERTENSION ATTRIBUTES

(71) Applicant: Anumana, Inc., Cambridge, MA (US)

(72) Inventors: Samir Awasthi, Boston, MA (US); Rakesh Barve, Bengaluru (IN); Shahir Asfahan, Bengaluru (IN); Shashi Kant, Bengaluru (IN); Ausath G. Anto, Thuckalay (IN)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/771,678

(22) Filed: Jul. 12, 2024

(65) Prior Publication Data

US 2026/0018304 A1 Jan. 15, 2026

(51) Int. Cl.

*G16H 50/50* (2018.01)
*A61B 5/00* (2006.01)
*A61B 5/021* (2006.01)
*G16H 10/60* (2018.01)

(52) U.S. Cl.

CPC ............ *G16H 50/50* (2018.01); *A61B 5/021* (2013.01); *A61B 5/7221* (2013.01); *A61B 5/748* (2013.01); *G16H 10/60* (2018.01)

(58) Field of Classification Search

CPC ........ G16H 50/50; G16H 10/60; A61B 5/021; A61B 5/7221; A61B 5/748

See application file for complete search history.

(56) References Cited

U.S. PATENT DOCUMENTS

| | | | | |
|---|---|---|---|---|
| 11,456,080 | B1 * | 9/2022 | Jain | A61B 5/4815 |
| 11,717,177 | B2 * | 8/2023 | Chegani | A61B 5/681 600/485 |
| 2015/0332012 | A1 * | 11/2015 | Edelson | A61B 5/7275 705/2 |
| 2019/0357854 | A1 * | 11/2019 | Reich | G16H 50/50 |

(Continued)

FOREIGN PATENT DOCUMENTS

| | | | | |
|---|---|---|---|---|
| CN | 116092701 | A * | 5/2023 | G16H 80/00 |
| EP | 0896282 | A1 | 2/1999 | |

(Continued)

OTHER PUBLICATIONS

Becker et al., From heterogeneous healthcare data to disease-specific biomarker networks: A hierarchical Bayesian network approach, Feb. 12, 2021, PLOS Computational Biology, pp. 1-21. (Year: 2021).*

(Continued)

*Primary Examiner* — Christopher L Gilligan
(74) *Attorney, Agent, or Firm* — CALDWELL LLC

(57) ABSTRACT

An apparatus and method for detecting hypertension attributes in a patient time-series data includes at least a processor and a memory communicatively connected to the at least a processor. The memory instructs the processor to receive a patient time-series data associated with a patient, input the patient time-series data into a hypertension panel wherein the hypertension panel comprises of a plurality of hypertension models, generate the hypertension attribute from the hypertension panel as a function of the patient time-series data and a hypertension model, and generate a confidence score from the hypertension panel as a function of the patient time-series data and the hypertension model.

20 Claims, 10 Drawing Sheets

(56) References Cited

U.S. PATENT DOCUMENTS

| | | | | |
|---|---|---|---|---|
| 2021/0100455 | A1* | 4/2021 | Deng | G16H 40/67 |
| 2021/0153750 | A1* | 5/2021 | Lu | A61B 5/021 |
| 2021/0282656 | A1* | 9/2021 | Li | A61B 5/1495 |
| 2022/0104715 | A1* | 4/2022 | Ogawa | A61B 5/0022 |
| 2022/0280121 | A1* | 9/2022 | Shivpure | A61B 5/7264 |
| 2022/0296111 | A1* | 9/2022 | Leabman | A61B 5/681 |
| 2023/0082362 | A1* | 3/2023 | Varadan | A61B 5/7278 600/301 |
| 2023/0263411 | A1* | 8/2023 | Stockmann | A61B 5/0215 600/490 |
| 2024/0268766 | A1* | 8/2024 | Kawabata | A61B 5/0205 |

FOREIGN PATENT DOCUMENTS

| | | | |
|---|---|---|---|
| KR | 20230169577 | A | 12/2023 |
| WO | 2022125806 | A1 | 6/2022 |
| WO | 2023057200 | A1 | 4/2023 |
| WO | WO-2023239960 | A1 * | 12/2023 |
| WO | 2024050307 | A1 | 3/2024 |

OTHER PUBLICATIONS

Chaurasia, Design and Implementation of Data Collection & Analysis Tool for Healthcare Parameter Monitoring using Inverse Low Pass Filter, Oct. 30, 2018, EAI Endorsed Transactions on Pervasive Health and Technology, vol. 4, Issue 16, pp. 1-12. (Year : 2018).*

* cited by examiner

APPARATUS AND METHOD FOR DETECTING HYPERTENSION ATTRIBUTES

FIELD OF THE INVENTION

The present invention generally relates to the field of machine learning. In particular, the present invention is directed to an apparatus and a method for detecting hypertension attributes in a patient time-series data.

BACKGROUND

Current systems used to detect hypertension require various inputs to generate resultant outputs. These systems are inefficient and require extensive human interaction and supervision. Additionally, current systems that may receive a singular input in order to output information associated with various diagnoses are inaccurate and prone to error.

SUMMARY OF THE DISCLOSURE

In an aspect, an apparatus for detecting hypertension attributes in a patient time-series data includes at least a processor and a memory communicatively connected to the at least a processor. The memory contains instructions configuring the processor to receive a patient time-series data associated with a patient, wherein the patient time-series data is captured using a measurement device, input the patient time-series data into a hypertension panel wherein the hypertension panel comprises of a plurality of hypertension models, generate the hypertension attribute from the hypertension panel as a function of the patient time-series data and a hypertension model, wherein the hypertension attribute comprises generating, using a first hypertension model, a first hypertension attribute comprising a measurement of the patient yielding a first hypertension level, generating, using a second hypertension model, a second hypertension attribute comprising a measurement of the patient yielding a second hypertension level, and generating the hypertension attribute using the patient time-series data and at least one of the first hypertension model and the second hypertension model and generating, using a second hypertension model, a second hypertension attribute comprising a measurement of the patient yielding a second hypertension level, and generate a confidence score from the hypertension panel as a function of the patient time-series data and at least one of the first hypertension model and the second hypertension model.

In another aspect, a method for detecting hypertension attributes in a patient time-series data includes receiving a patient time-series data associated with a patient, wherein the patient time-series data is captured using a measurement device, inputting the patient time-series data into a hypertension panel wherein the hypertension panel comprises of a plurality of hypertension models, generating the hypertension attribute from the hypertension panel as a function of the patient time-series data and a hypertension model, wherein the hypertension attribute comprises generating, using a first hypertension model, a first hypertension attribute comprising a measurement of the patient yielding a first hypertension level, generating, using a second hypertension model, a second hypertension attribute comprising a measurement of the patient yielding a second hypertension level, and generating the hypertension attribute using the patient time-series data and at least one of the first hypertension model and the second hypertension model and generating, using a second hypertension model, a second hypertension attribute comprising a measurement of the patient yielding a second hypertension level, and generating a confidence score from the hypertension panel as a function of the patient time-series data and at least one of the first hypertension model and the second hypertension model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatus and methods for detecting hypertension attributes in a patient time-series data. The apparatus includes at least a computing device comprised of a processor and a memory communicatively connected to the processor. The memory instructs the processor to receive a patient time-series data associated with a patient, wherein the patient time-series data is captured using a measurement device. The memory instructs the processor to input the patient time-series data into a hypertension panel wherein the hypertension panel comprises of a plurality of hypertension models. The memory instructs the processor to generate a hypertension attribute from the hypertension panel as a function of the patient time-series data and the hypertension model, wherein the hypertension attribute comprises generating, using a first hypertension model, a first hypertension attribute comprising a measurement of the patient yielding a first hypertension level, generating, using a second hypertension model, a second hypertension attribute comprising a measurement of the patient yielding a second hypertension level, and generating the hypertension attribute using the patient time-series data and at least one of the first hypertension model and the second hypertension model. The memory instructs the processor to generate a confidence score from the hypertension panel as a function of the patient time-series data and at least one of the first hypertension model and the second hypertension model.

Figure 1:
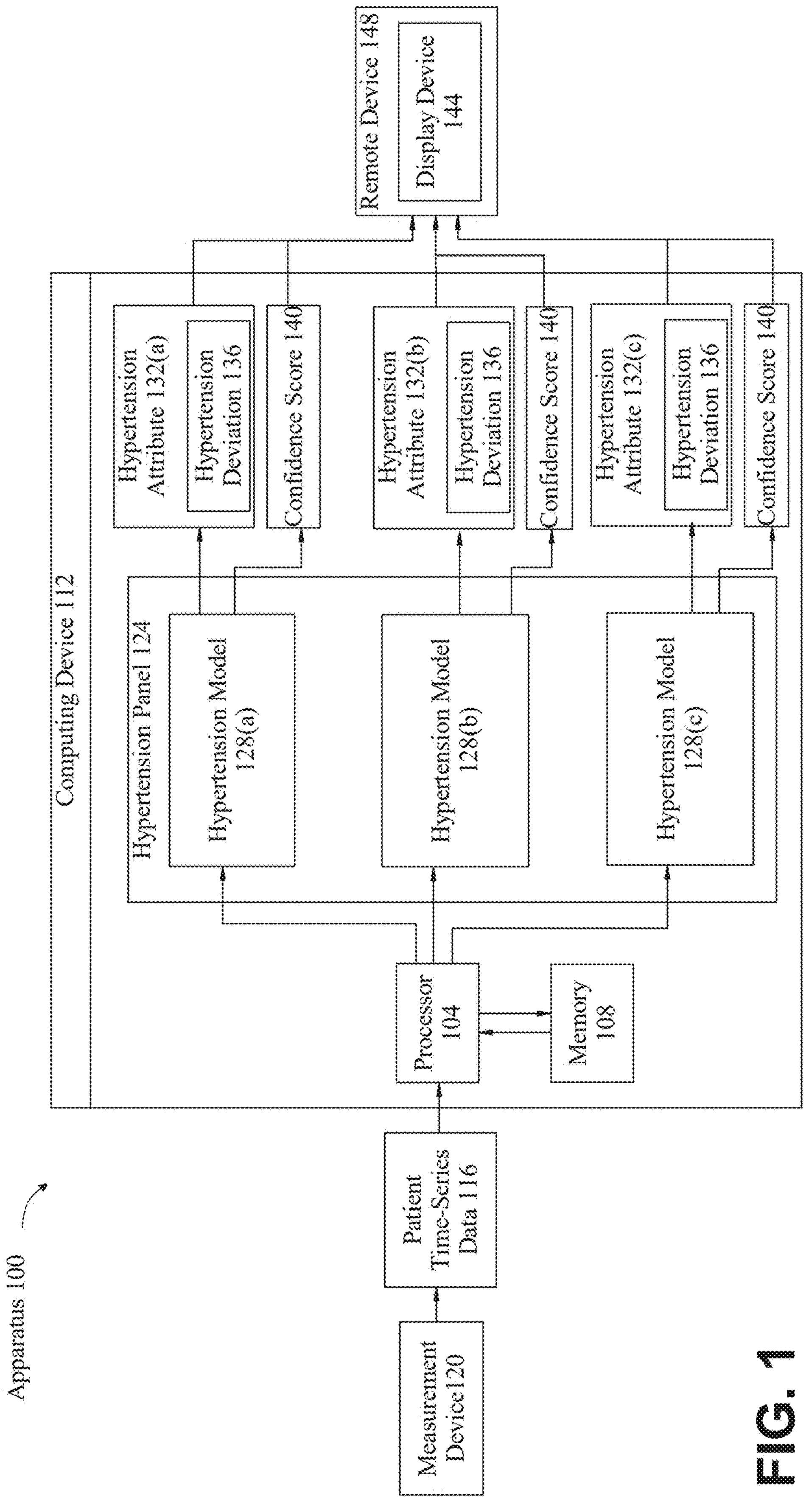
FIG. 1 is a block diagram of an apparatus for detecting hypertension attributes in a patient time-series data.

Referring now to FIG. 1, an exemplary embodiment of apparatus 100 for detecting hypertension attributes in a patient time-series data is illustrated. Apparatus 100 may include a processor 104 communicatively connected to a memory 108. As used in this disclosure, "communicatively connected" means connected by way of a connection, attachment, or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

Further referring to FIG. 1, apparatus 100 may include any "computing device" as described in this disclosure, including without limitation a microcontroller, microprocessor, digital signal processor (DSP) and/or system on a chip (SoC) as described in this disclosure. Apparatus 100 may include, be included in, and/or communicate with a mobile device such as a mobile telephone or smartphone. Apparatus 100 may include a single computing device 112 operating independently, or may include two or more computing devices 112 operating in concert, in parallel, sequentially or the like; two or more computing devices 112 may be included together in a single computing device 112 or in two or more computing devices 112. Apparatus 100 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices 112, and any combinations thereof. A network may employ a wired and/or a wireless mode of communication. In general, any network topology may be used. Information (e.g., data, software etc.) may be communicated to and/or from a computer and/or a computing device 112. Processor 104 may include but is not limited to, for example, a computing device 112 or cluster of computing devices 112 in a first location and a second computing device 112 or cluster of computing devices 112 in a second location. Apparatus 100 may include one or more computing devices 112 dedicated to data storage, security, distribution of traffic for load balancing, and the like. Apparatus 100 may distribute one or more computing tasks as described below across a plurality of computing devices 112 of computing device 112, which may operate in parallel, in series, redundantly, or in any other manner used for distribution of tasks or memory between computing devices 112. Apparatus 100 may be implemented, as a non-limiting example, using a "shared nothing" architecture.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Still referring to FIG. 1, processor 104 receives patient time-series data 116 associated with a patient and patient time-series data 116 is captured using measurement device 120. As used in this disclosure, a "patient time-series data" is information associated with a patient that is collection of recorded over a series of time intervals and/or using a series of temporally spaced samples. This may include, without limitation, various types of signal data, such as analog signals, digital signals, time-series signal data, spatial signals, frequency signals, multi-dimensional signals, and the like. In a non-limiting example, an analog signal is any continuous-time signal representing some other quantity, i.e., analogous to another quantity. For example, and without limitation, in an analog audio signal, the instantaneous signal voltage varies continuously with the pressure of the sound waves. Typically, analog signal refers to electrical signals; however, mechanical, pneumatic, hydraulic, and other systems may also convey or be considered analog signals. In another non-limiting example, a digital signal is a signal that represents data as a sequence of discrete values; at any given time it can only take on, at most, one of a finite number of values. In some cases, digital signals may represent information in discrete bands of analog levels, wherein all levels within a band of values represent the same information state. In a non-limiting example, a digital signal may be represented as a digital circuit. Typically, digital circuit signals can have two possible valid values; a binary signal or logic signal wherein the binary signal and the logic signal are represented by two voltage bands: one voltage band that is near a reference value, and the other voltage value that is near the supply voltage. The voltage bands correspond to the two values "zero" and "one" (or "false" and "true") of the Boolean domain, wherein at any given time, a binary signal represents one binary digit (bit). Without limitation, digital signals are generally used for communications and processing within electronic devices and computer systems. In another non-limiting example, time-series signal data is information in the form of a signal that is collected and recorded over consistent intervals of time. Without limitation, time-series signal data may be used in order to extract meaningful statistics and other characteristics of the data. Time-series signal data can be classified into two main types: continuous-time series signals and discrete-time signals. Continuous-time signals are signals that are measured and recorded over a continuous range, including, but not limited to, analog signals, such as sound waves and temperature measurements (from analog devices like analog thermometers). On the other hand, discrete-time signals are recorded at specific, distinct points. For example, and without limitation, discrete-time signals may include digital sensor measurements and financial market data sampled at fixed intervals. In another non-limiting example, patient time-series data 116 may include an electrocardiogram signal wherein the electrocardiogram signal may include an electrocardiogram datum. As used herein, an "electrocardiogram datum" is a single data point obtained from the electrical activity of the heart of a patient. An electrocardiogram datum may be derived from an electrocardiogram signal. In some embodiments, an electrocardiogram datum may include a rhythm strip electrocardiogram datum. As used herein, a "rhythm strip electrocardiogram datum" is a datum describing electrical activity detected using a single electrode. In some embodiments, an electrocardiogram datum may include a median beat electrocardiogram datum. As used herein, a "median beat electrocardiogram datum" is a datum describing electrical activity detected using a plurality of leads and/or electrodes. In some embodiments, an electrocardiogram datum may include data collected by 2, 3, 4, 5, 6, 7, 8, 9, 10, 11, 12, or more electrocardiogram leads. For example, an electrocardiogram datum may include a median beat collected by 12 electrocardiogram leads. A "lead," as used in this disclosure, is one or more electrodes attached to the skin to detect a heart's electric signals. As used in this disclosure, a "standard 12-lead electrocardiogram signal" is a measurement the electrical activity of a heart from 12 different perspectives. In a non-limiting embodiment a standard 12-lead electrocardiogram signal may include a graphical record of the direction and magnitude of the electrical activity generated by the depolarization and repolarization of the atria and ventricles of the heart.

With continued reference to FIG. 1, patient time-series data 116 may include temporal data, and metadata. As used in this disclosure, a "temporal data" is information which is collected and/or recorded over a continuous-time interval or discrete-time interval. Temporal data captures signal data changes over time and provides time-stamped data recordation. As used in the current disclosure, "metadata" refers to descriptive or informational data that provides details about the digital electrocardiogram data. Metadata may include descriptive metadata, wherein descriptive metadata is configured to describe the content, context, and structure of the data. In an embodiment, metadata may include data regarding the lead system the digital electrocardiogram data was recording. Electrocardiograms are typically recorded using multiple leads, each of which provides a different view of the heart's electrical activity. Common lead systems include the 12-lead, 6-lead, 3-lead, and single-lead electrocardiograms. The specific lead system used to generate the digital electrocardiogram data and their configurations may be documented in the metadata. In some embodiments, metadata associated with the digital electrocardiogram data may include information such as time, geographic location, medical facility names, medical professional logs, patient names, patient IDs, patient data, along with any other patient specific data. Metadata may be used to describe records of how the data has been accessed, utilized, or modified over time, aiding in understanding data usage patterns, and optimizing access.

With continued reference to FIG. 1, patient time-series data 116 may include electrocardiogram signals. As used in the current disclosure, a "electrocardiogram signal" is a signal representative of electrical activity of heart. The electrocardiogram signal may consist of several distinct waves and intervals, each representing a different phase of the cardiac cycle. These waves may include the P-wave, QRS complex, T wave, U wave, and the like. The P-wave may represent atrial depolarization (contraction) as the electrical impulse spreads through the atria. The QRS complex may represent ventricular depolarization (contraction) as the electrical impulse spreads through the ventricles. The QRS complex may include three waves: Q wave, R wave, and S wave. The T-wave may represent ventricular repolarization (recovery) as the ventricles prepare for the next contraction. The U-wave may sometimes be present after the T wave, it represents repolarization of the Purkinje fibers. The intervals between these waves provide information about the duration and regularity of various phases of the cardiac cycle. The electrocardiogram signal can help diagnose various heart conditions, such as arrhythmias, myocardial infarction (heart attack), conduction abnormalities, and electrolyte imbalances. In an embodiment, patient time-series data 116 is captured using measurement device 120.

With continued reference to FIG. 1, as used in this disclosure, a "measurement device" is any device that is able to extract any kind of data from a patient. In a non-limiting embodiment, measurement device 120 may include a transducer. As used in this disclosure, a "transducer" is a device used to transform one kind of energy into another. When a transducer converts a quantity of energy to an electrical voltage or an electrical current it is called a sensor. A measurable quantity of energy may include sound pressure, optical intensity, magnetic field intensity, thermal pressure, etc. When a transducer converts an electrical signal into another form of energy such as sound, light, mechanical movement, it is called an actuator. It should be noted that sound is incidentally a pressure field. Actuators allow the use of feedback at the source of the measurements. In a non-limiting embodiment, a transducer may detect at least a cardiac phenomenon and output patient time-series data 116.

In another non-limiting example, a transducer may include a plurality of clinical transducers. As used in this disclosure, a "plurality of clinical transducers" is a transducer device used in the medical field to measure, analyze, and/or quantify electrical signals in a body. Plurality of clinical transducers may generate training data for apparatus 100 and training data may be stored in an electronic health record database as described in more detail below. In a non-limiting embodiment, training data may include de-identified health records.

With continued reference to FIG. 1, measurement device 120 may be considered as a component or with a collection of electronics such as amplifiers, decoders, filters, computer devices a transducer. For the purposes of this disclosure an "instrument" is a sensor bundled with its associated electronics. However, in some embodiments, sensors may be further integrated with a transducer. Sensors may be integrated with wearable electrocardiogram devices such as, without limitation, electrocardiogram monitoring watches, bio stickers, portable electrocardiogram measuring devices, and the like.

With continued reference to FIG. 1, measurement device 120 integrated with a transducer may be linear so that response y to a stimulus x is in the form: y(x)=Ax, $0 \leq x \leq x_{max}$, A>0. It should be noted, there is a presumption that the stimulus to be positive. A is the sensitivity of the transducer gain, or the gain of the sensor. The gain is presumed to be positive for which the linear model satisfies the definition of linearity: y(x+z)=A(x+z)=y(x)+y(z). It should be noted that this example is an idealized form of measurement device 120 and may extend beyond the linearity constraints which may include time dependency, memory, and its output keeping track of input. A more generalized sensor may include the steady state transfer function of the sensor. For this case, the sensitivity can be defined as the derivative of the output with respect to the input:

$$S = \frac{\partial y}{\partial x}.$$

In this example, the sensor exhibits sensitivities to other operating parameters (i.e., supply voltage) or temperature. For the purposes of this disclosure, "sensitivity" is the ratio of output to input. This can include electrical output and signal input or an input transducer. It can also include physical output to an electrical input, or an output transducer. Sensitivity can also be used in its usual electrical meaning. In this it would refer to a percent change of a property of a device because of a percent change in a parameter. In some embodiments this would be a percent change in gain as a result of percent change in ambient temperature. This type of sensitivity may be referred to as the Gain of a sensor.

Still referring to FIG. 1, a transducer with integrated sensors may not respond to arbitrarily small signals. A transducer may respond to signals within a specified range from zero to a sensor threshold which does not cause the output of the sensor to change. The existence of a threshold relates to the nonlinear behavior of the device and the noise. A transducer with an integrated sensor may fail to respond to stimuli which are arbitrarily large as well. In this case, a transducer integrated with measurement device 120 may have a max range. The full range of a transducer integrated with measurement device 120 may be limited by compression or clipping. Compression and clipping are results of nonlinearity and thus may include a transducer as a nonlinearity device.

Still referring to FIG. 1, referring to the linear equation above assuming a linear sensor is improved with the addition of a constant: $y(x)=b_0+Ax$. It should be noted that the equation is not linear even though it is described as a first order polynomial. The constant is called a zero offset and can be defined in two ways: a sensor reading when the input is zero, or the value of the stimulus required to make the output zero. The zero offset is corrected by subtracting $b_0$ from y and recovering the linear description of a sensor: $y'(x)=y(x)-b_0=Ax$.

With continued reference to FIG. 1, a transducer may include very fast measurements where it can internally store energy. A transducer output may depend on previous measurements the integrated sensors make. It should be noted that the sensor may exhibit memory. The time dependence of measurement device 120 can be linear if the response is described by a linear differential equation:

$$\sum_{n=0}^{N} A_n \frac{\partial^n y}{\partial t^n} = \sum_{k=0}^{k} B_k \frac{\partial^k x}{\partial t^k}.$$

Taking the Laplace transform of this equation:

$$y(s, X) = \left( \frac{\sum_{k=0}^{K} B_k S^k}{\sum_{n=0}^{N} A_n S^n} \right) x = H(s)X(s),$$

which is in Laplace transform space and the sensor response is still linear in stimulus x. The response of measurement device 120 with a transfer function H(s) at time t is the convolution integral between the history of the stimulus x and the inverse Laplace transform h(t) of $$H(s)\colon\ y(t) = \int_0^\infty h(\tau)x(t-\tau)d\tau.A$$

transducer may behave like a low pass filter, wherein there is a delayed response to their input. There is a limit to the maximum stimulus frequency that can be detected. The maximum frequency measurement device 120 can interpret is approximately the inverse of its response time. In a nonlimiting example, measurement device 120 may include imaging devices, ultrasound device, echocardiogram devices, electrocardiogram devices, electroencephalogram devices, and the like.

With continued reference to FIG. 1, patient time-series data 116 may include a matrix. In an embodiment, the matrix may be represented by vectors. As used in this disclosure, a "vector" is a data structure that represents one or more quantitative values and/or measures the position vector. Such vector and/or embedding may include and/or represent an element of a vector space; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. A vector may be represented as an n-tuple of values, where n is one or more values, as described in further detail below; a vector may alternatively or additionally be represented as an element of a vector space, defined as a set of mathematical objects that can be added together under an operation of addition following properties of associativity, commutativity, existence of an identity element, and existence of an inverse element for each vector, and can be multiplied by scalar values under an operation of scalar multiplication compatible with field multiplication, and that has an identity element is distributive with respect to vector addition, and is distributive with respect to field addition. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent, for instance as measured using cosine similarity as computed using a dot product of two vectors; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes. A two-dimensional subspace of a vector space may be defined by any two orthogonal vectors contained within the vector space. Two-dimensional subspace of a vector space may be defined by any two orthogonal and/or linearly independent vectors contained within the vector space; similarly, an n-dimensional space may be defined by n vectors that are linearly independent and/or orthogonal contained within a vector space. A vector's "norm" is a scalar value, denoted $\|a\|$ indicating the vector's length or size, and may be defined, as a non-limiting example, according to a Euclidean norm for an n-dimensional vector a as:

$$\|a\| = \sqrt{\sum_{i=0}^{n} a_i^2}$$

In an embodiment, and with continued reference to FIG. 1, hypertension attributes 132*a-c* of patient time-series data 116 may be represented by a dimension of a vector space; as a non-limiting example, each element of a vector may include a number representing an enumeration of co-occurrences of first hypertension attribute 132 represented by the vector with second hypertension attribute 132. Hypertension attribute 132 may include hypertension. Hypertension attribute 132 may include hypertensive heart disease. As used in this disclosure, a "hypertension attribute" is a characteristic of a signal that is derived from the electroactivity of a patient's heart and related to the patient's blood pressure levels. Hypertension attributes 132*a-c* may include information related to a frequency domain feature. A frequency domain feature may include information about the frequency distributions that are present in an ECG signal. Hypertension attributes 132*a-c* may describe either a static signal or a particular time period of a dynamic signal. Hypertension attributes 132*a-c* may be obtained from a signal by analyzing the composition of the signal frequencies to identify unique patterns and/or irregularities in the signal. Without limitation, hypertension attributes 132*a-c* may include power spectral density, and the like. Alternatively, or additionally, dimensions of vector space may not represent distinct hypertension attributes 132*a-c*, in which case elements of a vector representing a first hypertension attribute 132 may have numerical values that together represent a geometrical relationship to a vector representing a second hypertension attribute 132, wherein the geometrical relationship represents and/or approximates a semantic relationship between the first hypertension attribute 132 and the second hypertension attribute 132. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below.

Any vectors as described herein may be scaled, such that each vector represents each attribute along an equivalent scale of values. In an embodiment associating hypertension attributes 132*a-c* to one another as described above may include computing a degree of vector similarity between a vector representing hypertension attributes 132*a-c* and a vector representing another hypertension attributes 132*a-c*; vector similarity may be measured according to any norm for proximity and/or similarity of two vectors, including without limitation cosine similarity. As used in this disclosure "cosine similarity" is a measure of similarity between two-non-zero vectors of a vector space, wherein determining the similarity includes determining the cosine of the angle between the two vectors. Cosine similarity may be computed as a function of using a dot product of the two vectors divided by the lengths of the two vectors, or the dot product of two normalized vectors. For instance, and without limitation, a cosine of 0° is 1, wherein it is less than 1 for any angle in the interval $(0,\pi)$ radians. Cosine similarity may be a judgment of orientation and not magnitude, wherein two vectors with the same orientation have a cosine similarity of 1, two vectors oriented at 90° relative to each other have a similarity of 0, and two vectors diametrically opposed have a similarity of −1, independent of their magnitude. As a non-limiting example, vectors may be considered similar if parallel to one another. As a further non-limiting example, vectors may be considered dissimilar if orthogonal to one another. As a further non-limiting example, vectors may be considered uncorrelated if opposite to one another. Additionally, or alternatively, degree of similarity may include any other geometric measure of distance between vectors.

Patient time-series data 116 may use a matrix to represent variables and/or parameters of the statistical model. As used in this disclosure "matrix" is a rectangular array or table of numbers, symbols, expressions, vectors, and/or representations arranged in rows and columns. For instance, and without limitation, matrix may include rows and/or columns comprised of vectors representing hypertension attributes 132*a-c*, where each row and/or column is a vector representing a distinct hypertension attribute 132; hypertension attributes 132*a-c* represented by vectors in matrix may include all frequency bands over a range of frequencies as described above as the statistical model identifies the hypertension attribute 132, including without limitation the magnitude and phase of a set of sinusoids at the frequency components of the signal as described above. As a non-limiting example matrix may include how a signal is distributed within different frequency bands over a range of frequencies.

A matrix may be generated by performing a singular value decomposition function. As used in this disclosure a "singular value decomposition function" is a factorization of a real and/or complex matrix that generalizes the eigen decomposition of a square normal matrix to any matrix of m rows and n columns via an extension of the polar decomposition. For example, and without limitation singular value decomposition function may decompose a first matrix, A, comprised of m rows and n columns to three other matrices, U, S, T, wherein matrix U, represents left singular vectors consisting of an orthogonal matrix of m rows and m columns, matrix S represents a singular value diagonal matrix of m rows and n columns, and matrix VT represents right singular vectors consisting of an orthogonal matrix of n rows and n columns according to the vectors consisting of an orthogonal matrix of n rows and n columns according to the function:

$$A_{m\times n} = U_{m\times m} S_{m\times n} V^T_{n\times n}$$

singular value decomposition function may find eigenvalues and eigenvectors of $AA^T$ and $A^TA$. The eigenvectors of $A^TA$ may include the columns of $V^T$, wherein the eigenvectors of $AA^T$ may include the columns of U. The singular values in S may be determined as a function of the square roots of eigenvalues $AA^T$ or $A^TA$, wherein the singular values are the diagonal entries of the S matrix and are arranged in descending order. Singular value decomposition may be performed such that a generalized inverse of a non-full rank matrix may be generated.

Still referring to FIG. 1, processor 104 inputs patient time-series data 116 into hypertension panel 124, wherein hypertension panel 124 includes a plurality of hypertension models 124. As used in this disclosure, a "hypertension panel" is a set of algorithms or machine learning models that are used to evaluate and monitor a patient's blood pressure. For example, and without limitation, hypertension panel 124 may include a set of algorithms configured to receive electrocardiogram signals associated with a patient. In one or more embodiments, hypertension panel 124 may be configured to provide a comprehensive view of a patient's journey through a heart condition. For example, and without limitation, hypertension panel 124 may include algorithms configured to receive electrocardiogram signals and output information associated with heart conditions such as but not limited to elevated blood pressures, hypertension stage 1 and stage 2, uncontrolled hypertension, and the like. In one or more embodiments, algorithms may include machine learning models, linear regression models and/or any other mathematical models configured to receive a variable such as patient time-series data 116 (e.g., electrocardiogram input data) and output a medical condition and/or information that may be indicative of a medical condition. In one or more embodiments, hypertension panel 124 may contain a distinct set of algorithms configured to monitor and/or generate a patient's health in association with a particular disease. For example, and without limitation, a first hypertension panel may be used to monitor hypertension in a patient wherein the first hypertension panel may output the percentage of blood leaving the heart whereas a second hypertension panel may be used to monitor a degree of heart arrythmia associated with the patient. In one or more embodiments, hypertension panel 124 may be used to monitor and/or determine a particular heart disease associated with patient such as but not limited to, arrythmias, tachycardia, bradycardia, heart attacks, coronary heart disease and the like. In one or more embodiments, hypertension panel 124 may be configured to receive the same or similar inputs and output differing results. In one or more embodiments, hypertension panel 124 may receive patient time-series data 116, and output a differing heart disease or heart condition.

With continued reference to FIG. 1, as used in this disclosure, a "hypertension model" is an individual system, algorithm module, and/or machine learning model used to evaluate and monitor a patient's blood pressure. Without limitation, hypertension models 128*a-c* may be trained using data from a plurality of clinical transducers, electronic health records, and the like. In one or more embodiment, hypertension models 128*a-c* may be trained on the training data in any manner described herein. In a non-limiting example, hypertension models 128*a-c* may include a statistical model, wherein the statistical model determines whether specific hypertension attributes 128 are present in patient time-series data 116. As used in this disclosure, a "statistical model" is a mathematical representation of relationships observed in data. A statistical model may provide insight on data regarding specific patterns and the like. A statistical model may describe, analyze, and make predictions based on the input data.

With continued reference to FIG. 1, in a non-limiting example, hypertension models 128*a-c* may be the same or substantially the same as the models described in U.S. patent application Ser. No. 16/754,007, filed on Apr. 6, 2020, titled "ECG-BASED EJECTION-FRACTION SCREENING," which is incorporated by reference herein in its entirety. In a non-limiting example, hypertension models 128*a-c* may be the same or substantially the same as the models described in U.S. patent application Ser. No. 17/275,276, filed on Mar. 11, 2021, titled "NEURAL NETWORKS FOR ATRIAL FIBRILLATION SCREENING," which is incorporated by reference herein in its entirety. In a non-limiting example, hypertension models 128*a-c* may be the same or substantially the same as the models described in U.S. patent application Ser. No. 17/500,287, filed on Oct. 13, 2021, titled "NONINVASIVE METHODS FOR DETECTION OF PULMONARY HYPERTENSION," which is incorporated by reference herein in its entirety. In a non-limiting example, hypertension models 128*a-c* may be the same or substantially the same as the models described in U.S. patent application Ser. No. 18/648,292, filed on Apr. 26, 2024, titled "METHOD AND AN APPARATUS FOR DETECTING A LEVEL OF CARDIOVASCULAR DISEASE," which is incorporated by reference herein in its entirety. In a non-limiting example, hypertension models 128*a-c* may be the same or substantially the same as the models described in U.S. patent application Ser. No. 18/642,200, filed on Apr. 28, 2023, titled "ARTIFICIAL-INTELLIGENCE ENHANCED SCREENING FOR CARDIAC AMYLOIDOSIS BY ELECTROCARDIOGRAPHY," which is incorporated by reference herein in its entirety.

Figure 6:
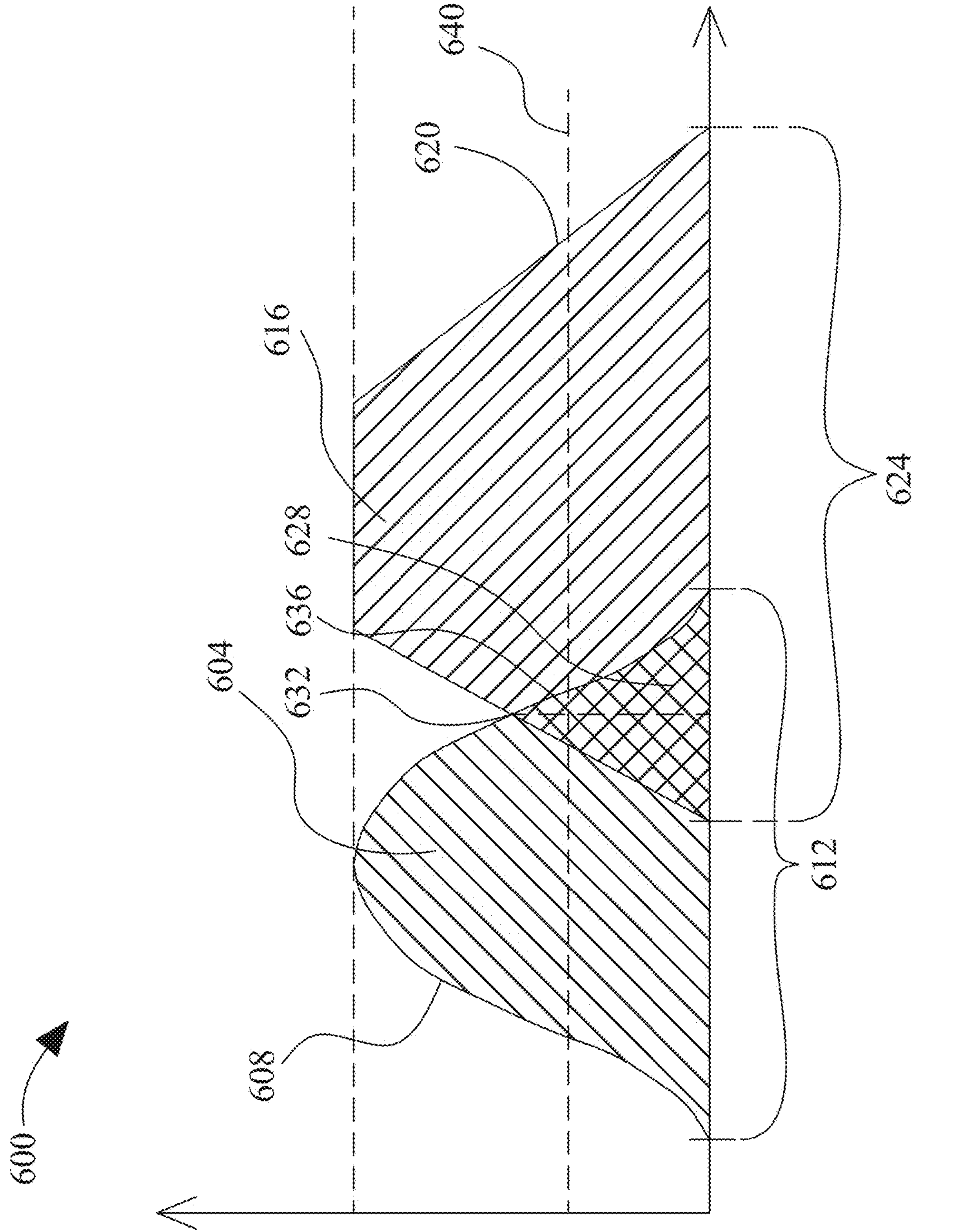
FIG. 6 is an illustration of an exemplary embodiment of fuzzy set comparison.

With continued reference to FIG. 1, hypertension models 128*a-c* may include a fuzzy set comparison model as described in more detail in FIG. 6. In a no-limiting example, the fuzzy set comparison model may include a fuzzy inference model. As used in this disclosure, a "fuzzy inference model" uses fuzzy logic to reach a decision and derive a meaningful outcome. In a non-limiting example, fuzzy inference system may be associated with degrees of hypertension levels, such as, "elevated blood pressure," "stage 1 hypertension," "stage 2 hypertension," and "critical hypertension." In some embodiments, an inferencing rule may be applied to determine fuzzy set membership of a combined output based on fuzzy set membership of linguistic variables. In a non-limiting example, membership of a combined output in an "elevated blood pressure" fuzzy set may be determined based on a percentage membership of a second linguistic variable with a first mode in an "elevated blood pressure" fuzzy set and a percentage membership of a second linguistic variable associated with a second mode in a "stage 1 hypertension" fuzzy set. In some embodiments, hypertension panel parameters may then be determined by comparison to a threshold or output using another defuzzification process. Each stage of such a process may be implemented using any type of machine learning model such as any type of neural network described herein. In some embodiments parameters of one or more fuzzy sets may be tuned using machine learning. In one or more embodiment, fuzzy inferencing and/or machine learning may be used to synthesize the outputs of a plurality of hypertension models, for example, in some cases, the output (e.g., hypertension attribute 132*a-c*), may be combined to make an overall or final determination, which may be displayed with or instead of individual outputs. In another non-limiting example, the outputs may compete, for example, the output with the highest confidence score 140 may be the output displayed at remote device 148, or displayed first in a ranked display of result outputs.

Figure 3:
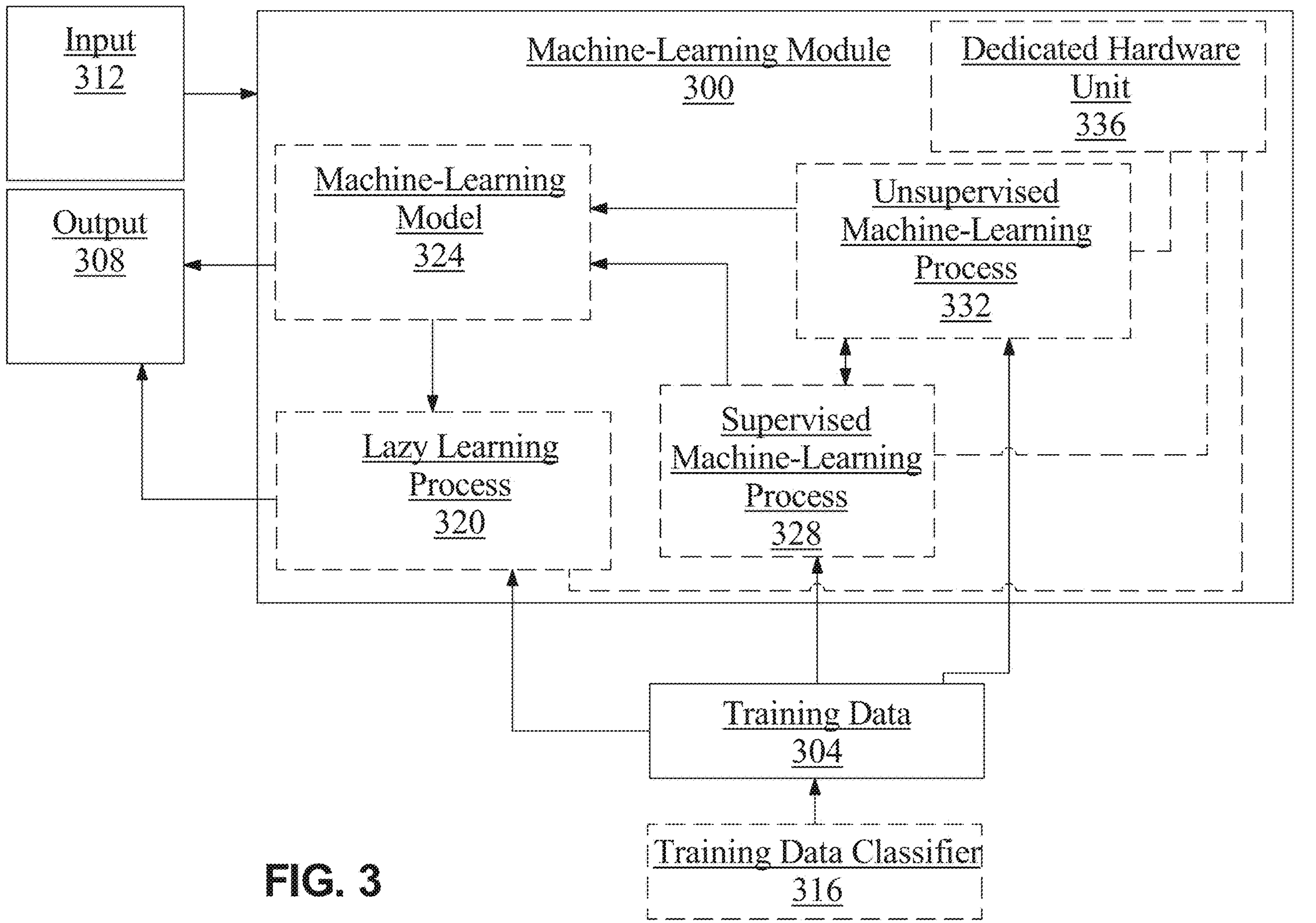
FIG. 3 is a block diagram of an exemplary machine-learning process.

Alternatively or additionally, hypertension models 128*a-c* may include a machine learning model as described in more detail in FIG. 3. Alternatively or additionally, the machine learning model as described in FIG. 3 may include a neural network as detailed in FIG. 4 and FIG. 5. The machine learning model may also include a convolutional neural network. In an embodiment, specific signal characteristics may be extracted by utilizing deep neural networks, which may learn and identify complex patterns and features in the ECG signals that may not be immediately apparent through traditional analysis methods. In some embodiments, the machine learning model may include a classifier.

With continued reference to FIG. 1, hypertension attribute may include information associated with the function of a patient's heart. For example, and without limitation, hypertension attributes 132*a-c* may include information associated with high blood pressure, such as 120/80 mm Hg. In one or more embodiments, hypertension attributes 132*a-c* may be used to determine a level or value associated with a particular heart condition. For example, and without limitation, hypertension attributes 132*a-c* may include a hypertension level. In another non limiting example, hypertension attributes 132*a-c* may be used to determine how well a heart is functioning as a numerical value. In one or more embodiments, hypertension attributes 132*a-c* may include a level of probability associated with a heart condition, wherein the level of probability may indicate the probability that the patient has the condition currently, and/or the probability the patient will have the condition in the future. In one or more embodiments, hypertension attributes 132*a-c* may include, but is not limited to, characteristics used to indicate a level of atrial fibrillation, tachycardia, premature beats, bradycardia, heart block, heart palpitations and the like. In one or more embodiments, hypertension panel 120 may be configured to output differing hypertension attributes 132*a-c*. In one or more embodiments, hypertension attributes 132*a-c* may include the severity of the heart disease or heart condition. In one or more embodiments, the severity may be rated on a scale of 0 to 100 wherein a 0 may indicate that that there is no severity and 100 may indicate that the heart condition is quite severe. In one or more embodiments, hypertension attributes 132*a-c* may include numerical amounts associated with each condition wherein the numerical amount may indicate the severity of the condition and/or numerical amounts that can be compared to reference ranges in order to determine the severity of the heart condition. In one or more embodiments, hypertension attributes 128 may include vector loops indicating electrical signals within the heart, wherein vector loops may be used to determine the severity of the condition. In one or more embodiments, cardiac values may include P waves and QRS complexes which may be used to determine the severity of a condition.

With continued reference to FIG. 1, hypertension attributes 132*a-c* may include a hypertension level of the patient wherein the hypertension level may include a measurement of systolic and/or diastolic blood pressure levels. In one or more embodiments, high blood pressure levels may indicate the hearts ability to regulate blood pressure. In one or more embodiments, a blood pressure level of 120/80 mm Hg may indicate that the patient has normal blood pressure. In one or more embodiments, a blood pressure level with systolic readings between 120-129 and diastolic readings between 80-89 mm Hg may indicate that the patient has an elevated blood pressure. In one or more embodiments, a blood pressure level with systolic readings between 130-139 and diastolic readings between 80-89 mm Hg may indicate that the patient has stage 1 hypertension. In one or more embodiments, a blood pressure level with systolic reading of 140 and diastolic reading of 90 mm Hg or higher may indicate that the patient has stage 2 hypertension. In one or more embodiments, a blood pressure level of 180/120 mm Hg may indicate the patient is experiencing a hypertensive crisis, requiring immediate medical attention. In one or more embodiments, a determined hypertension level can be used to determine if emergency medical assistance is required prior to heart failure occurring. In one or more embodiments, hypertension attributes 132*a-c* may include a blood pressure level of the patient. In one or more embodiments, hypertension attributes 132*a-c* may include changes in the blood pressure level.

With continued reference to FIG. 1, in one or more embodiments, shape of an ECG waveform may be influenced by a number of factors. For example and without limitation, subtle deformations may be imparted on one or more portions of the ECG waveform for a patient who has high blood pressure as compared to another patient who has normal blood pressure levels. The underlying disease affecting the heart, whether due to atherosclerosis, myopathic processes, inflammation, valvular derangements from any cause, can impair the heart muscle's pumping capability. The underlying disease may similarly affect the metabolism of individual myocytes or their interconnections, and lead to deposition of fibrosis or infiltration of inflammatory cells, all of which lead to subtle electrical changes. These local cardiac electrical changes may contribute to deformations recorded on the surface ECG and/or within signal data 116. Such deformations may not be visible with the naked eye, but may nonetheless be detectable using computer-based models according to the techniques disclosed herein.

With continued reference to FIG. 1, hypertension panel 124 is configured to receive patient time-series data 116 as an input, calculate hypertension attributes 132*a-c*, and output hypertension attributes 132*a-c*. In a nonlimiting example, hypertension panel 124 may receive a patient time-series data 116, such as, without limitation, a patient's ECG data, and hypertension panel 124 may calculate hypertension attributes 132*a-c* based on the patient's ECG data, and output the attribute to a display device for the patient to understand their risk for hypertension and/or their current blood pressure and what that measurement reading means.

With continued reference to FIG. 1, plurality of hypertension models 132 may include a hypertension classifier model, a hypertension prediction model, and a hypertension correlation model, as described in more detail below. In a non-limiting example, hypertension models 128*a-c* may be the same or substantially the same as the system described in U.S. patent application Ser. No. 17/275,276, filed on Mar. 11, 2021, titled "NEURAL NETWORKS FOR ATRIAL FIBRILLATION SCREENING," which is incorporated by reference herein in its entirety. In a non-limiting example, hypertension models 128*a-c* may be the same or substantially the same as the system described in U.S. patent application Ser. No. 17/500,287, filed on Oct. 13, 2021, titled "NONINVASIVE METHODS FOR DETECTION OF PULMONARY HYPERTENSION," which is incorporated by reference herein in its entirety. In a non-limiting example, hypertension models 128*a-c* may be the same or substantially the same as the system described in U.S. patent application Ser. No. 17/552,246, filed on Dec. 15, 2021, titled "SYSTEMS AND METHODS FOR DIAGNOSING A HEALTH CONDITION BASED ON PATIENT TIME SERIES DATA," which is incorporated by reference herein in its entirety. In a non-limiting example, hypertension models 128*a-c* may be the same or substantially the same as the system described in U.S. patent application Ser. No. 17/073,230, filed on Oct. 16, 2020, titled "METHOD AND SYSTEM FOR MEASURING CARDIAC TISSUE HEALTH BASED ON DV/Dtmin OF A DEPOLARIZATION WAVE WITHIN A CARDIAC ELECTROGRAM," which is incorporated by reference herein in its entirety. In a non-limiting example, hypertension models 128*a-c* may be the same or substantially the same as the system described in U.S. patent application Ser. No. 17/073,239, filed on Oct. 16, 2020, titled "METHOD AND SYSTEM FOR MEASURING CARDIAC ELECTROGRAM DEPOLARIZATION VOLTAGE," which is incorporated by reference herein in its entirety. In a non-limiting example, hypertension models 128*a-c* may be the same or substantially the same as the system described in U.S. patent application Ser. No. 18/229,854, filed on Aug. 3, 2023, titled "IDENTIFICATION AND RISK STRATIFICATION OF CORONARY DISEASE BY ARTIFICIAL INTELLIGENCE-ENABLED ECG," which is incorporated by reference herein in its entirety. In a non-limiting example, hypertension models 128*a-c* may be the same or substantially the same as the system described in U.S. patent application Ser. No. 18/395,399, filed on Dec. 22, 2023, titled "METHODS AND APPARATUSES FOR SYNTHESIZING TIME SERIES DATA AND DIAGNOSTIC DATA," which is incorporated by reference herein in its entirety. In a non-limiting example, hypertension models 128*a-c* may be the same or substantially the same as the processing module described in U.S. patent application Ser. No. 18/592,680, filed on Mar. 1, 2024, titled "APPARATUS AND METHOD FOR TRAINING AN ARTIFICIAL INTELLIGENCE-SUPPORTED DIAGNOSTIC ASSESSMENT TOOL," which is incorporated by reference herein in its entirety. In a non-limiting example, hypertension models 128*a-c* may be the same or substantially the same as the processing module described in U.S. patent application Ser. No. 18/641,150, filed on Apr. 19, 2024, titled "APPARATUS AND METHODS FOR AUTOMATIC SUGGESTION OF ATRIAL FIBRILLATION CASES BASED ON A PRESENCE OF ABNORMAL PULMONARY VEIN ANATOMY", which is incorporated by reference herein in its entirety. In a non-limiting example, hypertension models 128*a-c* may be the same or substantially the same as the processing module described in U.S. patent application Ser. No. 18/771,472, filed on Jul. 12, 2024, titled "APPARATUS AND A METHOD FOR IDENTIFYING THE PROGRESSION OF CORONARY HEART DISEASE", which is incorporated by reference herein in its entirety.

With continued reference to FIG. 1, plurality of hypertension models may include a loss function. In one or more embodiments, hypertension models 128*a-c* may utilize a loss function in order to measure the discrepancy between predicted outputs of hypertension models 128*a-c* and the actual blood pressure reading in the patient. In one or more embodiments, hypertension models 128*a-c* may adjust parameters iteratively through optimization techniques such as, but not limited to gradient descent to minimize the discrepancy.

In one or more embodiments, a machine learning model, such as hypertension models 128*a-c*, may include parameter values. "Parameter values" for the purposes of this disclosure are internal variables that a machine learning model has generated from training data in order to make predictions. In one or more embodiments, parameter values may be adjusted during training or pretraining in order to minimize a loss function. In one or more embodiments, during training, predicted outputs of hypertension models 128*a-c* are compared to actual outputs wherein the discrepancy between predicted output and actual outputs are measured in order to minimize a loss function. A loss function also known an "error function" may measure the difference between predicted outputs and actual outputs in order to improve the performance of the machine learning model. A loss function may quantify the error margin between a predicted output and an actual output wherein the error margin may be sought to be minimized during the training process. The loss function may allow for minimization of discrepancies between predicted outputs and actual outputs of the machine learning model. In one or more embodiments, the loss function may adjust parameter values of the machine learning model. In one or more embodiments, in a linear regression model, parameter values may include coefficient assigned to each feature and the bias term. In one or more embodiments, in a neural network, parameter values may include weights and biases associated with the connection between neurons or nodes within layers of the network. In one or more embodiments, processor 104 may be configured to minimize a loss function by adjusting parameter values of hypertension models 128*a-c* based on discrepancies between predicted outputs and actual outputs. In one or more embodiments, processor 104 may be configured to iteratively pretrain hypertension models 128*a-c*, wherein processor 104 may be configured to iteratively receive patient time-series data 116 from patients and adjust parameter values of hypertension models 128*a-c*. In an embodiment, the more patient time-series data 116 received by hypertension models 128*a-c*, the more accurate the hypertension models 128*a-c* may be in predicting hypertension levels in the patient. In one or more embodiments, parameter values may correspond to learned features of patient time-series data 116, such as, without limitation, waveforms, patterns, frequencies and the like.

With continued reference to FIG. 1, apparatus 100 may include training hypertension models 128*a-c* which may include receiving a plurality of patient time-series data examples associated with a plurality of patients, pretraining hypertension models 128*a-c* in hypertension panel 124 as a function of plurality of patient time-series data examples by adjusting one or more parameter attributes of hypertension models 128*a-c*, and training hypertension models 128*a-c* as a function of the parameter attributes and electronic health records. As used in this disclosure, "electronic health records" refer to digital information related to a patient's medical history. Electronic health records may include de-identified information related a patient's medical diagnoses, medications, treatments, lab results, and any other related information. In an embodiment, electronic health records may include electrocardiogram data from a patient, wherein the electrocardiogram data may include a plurality of signals.

With continued reference to FIG. 1, hypertension attributes 132*a-c* may include a hypertension deviation 140, wherein the hypertension deviation 136 includes a change in hypertension attributes 132*a-c*. As used in this disclosure, a "hypertension deviation" is a change in hypertension attributes 132*a-c*. For example and without limitation, hypertension deviation 136 may indicate that a patients risk of heart attack has increased 15% (e.g., from 20% to 35%). In another non limiting example, hypertension deviation 136 may indicate a change in blood pressure wherein hypertension deviation 136 may indicate that the blood pressure of the patient has increased from 120/80 mm Hg to 130/80 mm Hg. In one or more embodiments, blood pressure levels may be indicated by the patient's blood pressure levels which is recorded using the systolic blood pressure and the diastolic blood pressure. The systolic blood pressure indicates how much pressure a patient's blood is exerting against their artery walls when the heart contracts and is represented by the first number of the blood pressure reading. The diastolic blood pressure indicates how much pressure the patient's blood is exerting against their artery walls while the heart muscles are resting between contractions and is represented by the second number of a blood pressure reading. For example, stage 2 hypertension may be recorded as 140/90 mm Hg or higher indicating that the heart is exerting an elevated pressure of 140 mm Hg of pressure against the patients artery walls when the heart contracts and 90 mm Hg of pressure against the patients artery walls when the heart is resting. In one or more embodiments, hypertension panel 124 may be configured to output blood pressure levels of the patient. In one or more embodiments, blood pressure levels may be determined by analyzing changes in waveforms associated with signals 116. In one or more embodiments, increased QRS complex, increased R wave amplitude, and increased S wave depth in specific leads may indicate left ventricular hypertrophy (LVH) which may be associated with a particular stage of hypertension. In one or more embodiments, hypertension panel 124 may receive patient time-series data 116 and determine a stage of hypertension in the patient. In one or more embodiments, hypertension deviation 136 may indicate a change in blood pressure levels, such as for example, an increase from 120/80 mm Hg to 130/80 mm Hg. In one or more embodiments, hypertension deviation 136 may be generated as a function of hypertension panel 124. In one or more embodiments, processor 104 may receive hypertension attributes 132*a-c* from a previous iteration and compare the previous hypertension attributes 132*a-c* to hypertension attribute 132 of a current iteration. In one or more embodiments, the change between the output of the previous iteration and the output of the current iteration may be used as hypertension deviation 140. In one or more embodiments, hypertension deviation 136 may be generated as a function of a comparison between previous patient time-series data 116 received and patient time-series data 116 received from the current iteration wherein changes between signals may indicate hypertension deviation 140. In one or more embodiments, hypertension deviation 136 may be visually displayed to a patient, such as through a graph depicting changes in hypertension attributes over time. In one or more embodiments, cardiac deviations 140 may be used to indicate to a patient how their health has increased or decreased since a previous appointment, visit, generation of hypertension attributes 132*a-c* and the like. In one or more embodiments, at least one hypertension attribute 132 may include hypertension deviation 136 wherein hypertension deviation 136 includes a change in hypertension attribute 132.

With continued reference to FIG. 1, hypertension deviation 136 may be used to predict future hypertension attributes and/or determine trends for hypertension attributes. In one or more embodiments, hypertension deviation 136 may be used to determine if a patient requires medication prior to experiencing a heart failure. In one or more embodiments, hypertension deviation 136 may be used to prevent various heart conditions before they occur. In one or more embodiments, hypertension deviation 136 may be used to determine if a particular medication or treatment is working due to changes in hypertension attributes.

Still referring to FIG. 1, processor 104 generates hypertension attributes 132*a-c* from hypertension panel 124 as a function of patient time-series data 116 and hypertension model 128*a-c*, wherein hypertension attributes 132*a-c* includes generating, using a first hypertension model, a first hypertension attribute which includes a measurement of the patient yielding a first hypertension level and generating, using a second hypertension model, a second hypertension attribute which includes a measurement of the patient yielding a second hypertension level, and generating hypertension attribute 132*a-c* using patient time-series data 116 and at least one of the first hypertension model and the second hypertension model. As used in this disclosure, a "hypertension level" is a range of blood pressure levels that are associated with particular hypertension categories. For example and without limitation, hypertension level may include a range of blood pressure levels ranging from 120-180 in the systolic measurement and around 50-90 in diastolic measurement. In one or more embodiments, a patient may yield a hypertension level by having a blood pressure within a range of the hypertension level. For example, and without limitation, a patient may yield a hypertension level of between 120/80 mm Hg and 125/85 mm Hg in instances in which the patient has a hypertension level of 122/84 mm Hg. In one or more embodiments, falling within a particular hypertension level may indicate an underlying heart disease. In one or more embodiments, falling within a particular hypertension level may indicate an underlying heart disease. In one or more embodiments, falling within a particular hypertension level may indicate an underlying heart disease. For example, and without limitation, a patient yielding a hypertension level of 120/80 mm Hg may indicate that the patient has a normal blood pressure level. For example, and without limitation, a patient yielding a hypertension level of between 120/80 mm Hg and 129/50 mm Hg may indicate that the patient has an elevated blood pressure. For example, and without limitation, a patient yielding a hypertension level of between 130/80 mm Hg and 139/89 mm Hg may indicate that the patient has hypertension stage 1. For example, and without limitation, a patient yielding a hypertension level of between 140/90 mm Hg and higher may indicate that the patient has hypertension stage 2. For example, and without limitation, a patient yielding a hypertension level over 180/120 mm Hg may indicate that the patient is experiencing a hypertensive crisis and requires medical attention immediately. In one or more embodiments, hypertension panel 124 may be configured to calculate hypertension attributes 132*a-c* for each hypertension level. For example, and without limitation, a first hypertension panel may be configured to determine a first hypertension attribute associated with a first hypertension level and a second hypertension panel may be used to determine a second hypertension attribute associated with a second hypertension level. In an embodiment, hypertension panel 124 may be configured to output a given value that the patient falls within a range of hypertension levels.

Still referring to FIG. 1, processor 104 generates confidence score 140 from hypertension panel 124 as a function of patient time-series datal 16 and hypertension models 128*a-c*. As used herein, a "confidence score" is a degree of confidence that hypertension attributes 132*a-c* are accurate. In some embodiments, confidence score 140 may be determined as a function of a machine learning model, such as hypertension models 128*a-c*. Confidence score 140 may be used to predict how likely hypertension models 128*a-c* output is to be accurate. For example, in some classifiers, numerical values are calculated, and a cutoff value is used to determine which category the input fits into. In this example, the numerical value may be used to determine a certainty score based on how closely it fits into a class and/or how close to a decision boundary it is. In another example, in clustering algorithms, certainty scores may be calculated based on how closely an input fits into a cluster. In some embodiments, hypertension attributes 132*a-c* are generated without the use of hypertension models 128*a-c*, and confidence score 140 is generated using other methods. Both hypertension attributes 132*a-c* and confidence score 140 may be displayed through display device 144 as described further below.

Still referring to FIG. 1, processor 104 may display, using display device 144 of remote device 148, hypertension attributes 132*a-c* through a graphical user interface. As used in this disclosure, a "display device" refers to an electronic device that visually presents information to an entity. In some cases, display device 144 may be configured to project or show visual content generated by computers, video devices, or other electronic mechanisms. In some cases, display device 144 may include a liquid crystal display (LCD), a cathode ray tube (CRT), a plasma display, a light emitting diode (LED) display, and any combinations thereof. In a non-limiting example, one or more display devices may vary in size, resolution, technology, and functionality. Display device 144 may be able to show any data elements and/or visual elements as listed above in various formats such as, textural, graphical, video among others, in either monochrome or color. Display device 144 may include, but is not limited to, a smartphone, tablet, laptop, monitor, tablet, and the like. Display device 144 may include a separate device that includes a transparent screen configured to display computer generated images and/or information. In some cases, display device 144 may be configured to present a graphical user interface (GUI) to a user, wherein a user may interact with the graphical user interface. In some cases, a user may view a graphical user interface through display device 144. Additionally, or alternatively, processor 104 be connected to display device 144. In one or more embodiments, transmitting hypertension attributes 132*a-c* may include displaying hypertension attributes 132*a-c* at display device 144 using a visual interface. As used in this disclosure, a "graphical user interface" is a graphical form of user interface that allows users to interact with electronic devices. In some embodiments, a graphical user interface may include icons, menus, other visual indicators or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in a graphical user interface. For example, links to decentralized platforms as described in this disclosure may be incorporated using icons. Using an icon may be a fast way to open documents, run programs etc. because clicking on them yields instant access.

With continued reference to FIG. 1, as used in this disclosure, a "remote device" is any device external to computing device 112. Remote device 148 may transmit a signal, bit, datum, and/or parameter to computing device 112. Remote device 148 may include display device 144. Remote device 148 may receive hypertension attributes 132*a-c* and/or confidence score 140. Remote device 148 may include interactive features, wherein user may engage with the information displayed on remote device 148.

With continued reference to FIG. 1, inputting patient time-series data 116 into hypertension panel 124 may include selecting hypertension models 128*a-c* from plurality of hypertension models 132 as a function of a user input and the graphical user interface. In a non-limiting embodiment the graphical user interface may include a data structure. As used in this disclosure, "data structure" is a way of organizing data represented in a specialized format on a computer configured such that the information can be effectively presented in a graphical user interface. In some cases, the data structure includes any input data. In some cases, the data structure contains data and/or rules used to visualize the graphical elements within a graphical user interface. In some cases, the data structure may include any data described in this disclosure. In some cases, the data structure may be configured to modify the graphical user interface, wherein data within the data structure may be represented visually by the graphical user interface. In some cases, the data structure may be continuously modified and/or updated by processor 104, wherein elements within graphical user interface may be modified as a result. In some cases, processor 104 may be configured to transmit display device the data structure. Transmitting may include, and without limitation, transmitting using a wired or wireless connection, direct, or indirect, and between two or more components, circuits, devices, systems, and the like, which allows for reception and/or transmittance of data and/or signal(s) therebetween. Data and/or signals there between may include, without limitation, electrical, electromagnetic, magnetic, video, audio, radio, and microwave data and/or signals, combinations thereof, and the like, among others. Processor 104 may transmit hypertension attributes 132*a-c*, as described above, to a database wherein hypertension attributes 132*a-c* may be accessed from the database. Processor 104 may further transmit hypertension attributes 132*a-c* display device 144, remote device 148, or another computing device 112.

With continued reference to FIG. 1, hypertension attributes 132*a-c* may include comparing hypertension attributes 132*a-c* to a target blood pressure level and displaying hypertension attributes 132*a-c* as a function of the comparison. As used in this disclosure, a target blood pressure level" is the ideal blood pressure of a healthy individual. The target blood pressure level may take various factors into account such as, but not limited to, the patient's age, sex, height, weight, and the like. In an embodiment, the target blood pressure level of a patient may be 120/80 mm Hg.

With continued reference to FIG. 1, graphical user 144 interface may generate a visual element associated with hypertension attributes 132*a-c*, wherein the visual element is further associated with an event handler. As used in this disclosure, a "visual element" is any individual component that expresses an idea and/or conveys a message. A visual element may include visual data such as, but not limited to, images, colors, shapes, lines, arrows, icons, photographs, infographics, text, any combinations thereof, and the like. A visual element may include any data transmitted to display device, client device, and/or graphical user interface. In some embodiments, visual element may be interacted with. For example, visual element may include an interface, such as a button or menu. In some embodiments, visual element may be interacted with using a user device such as a smartphone, tablet, smartwatch, or computer.

With continued reference to FIG. 1, as used in this disclosure, an "event handler" is a module, data structure, function, and/or routine that performs an action on remote device in response to a user interaction with event handler graphic. For instance, and without limitation, an event handler may record data corresponding to user selections of previously populated fields such as drop-down lists and/or text auto-complete and/or default entries, data corresponding to user selections of checkboxes, radio buttons, or the like, potentially along with automatically entered data triggered by such selections, user entry of textual data using a keyboard, touchscreen, speech-to-text program, or the like. Event handler may generate prompts for further information, may compare data to validation rules such as requirements that the data in question be entered within certain numerical ranges, and/or may modify data and/or generate warnings to a user in response to such requirements.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

Figure 2A:
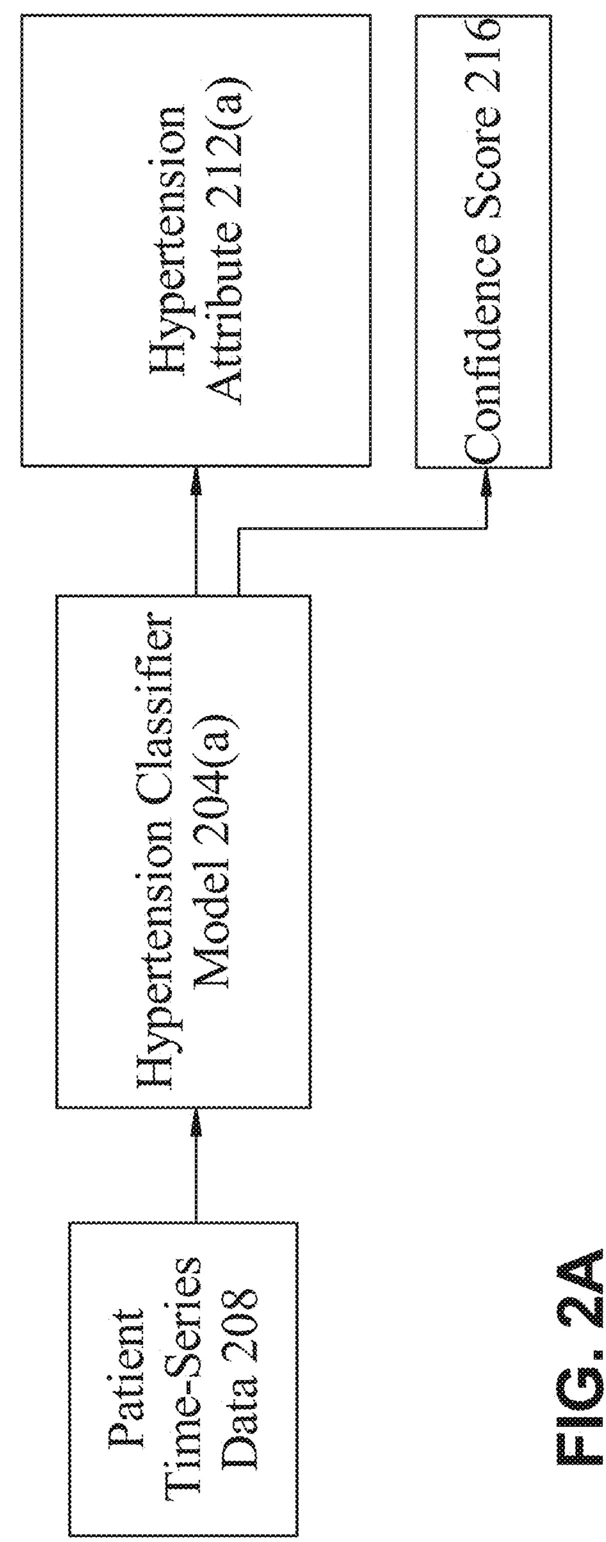
FIG. 2A is an exemplary embodiment of a system for instantiating a hypertension classifier model in accordance with the subject disclosure.

FIG. 2A is an exemplary embodiment of a system, 200*a*, for instantiating a hypertension classifier model in accordance with the subject disclosure. In one or more embodiments, system 200*a* may include hypertension classifier model, 204*a*. In one or more embodiments, hypertension classifier model 204*a* may be trained using patient time-series data 208. In one or more embodiments, hypertension classifier model 204*a* may output hypertension attribute 212*a* and confidence score 216. In one or more embodiments, hypertension classifier model 204*a* may identify and determine that patient time-series data 208 is associated with one or more hypertension levels, for example, without limitation, elevated blood pressure, stage 1 hypertension, stage 2 hypertension, critical hypertension. In one or more embodiments, hypertension classifier model 204*a* may classify patient time-series data 208 as either falling within a hypertension level or not, where if the patient does not yield a hypertension level, hypertension classifier model 204*a* may suggest a different diagnosis, such as, without limitation a heart disease and/or condition related to hypertension. In one or more embodiments, confidence score 216 may include an evaluation of the certainty of the hypertension based on various parameters. In one or more embodiments, confidence score 216 may include a rating of certainty on a scale of 1 through 5, where 1 is confident and 5 is not confident at all. In one or more embodiments, hypertension attribute 212*a* and/or confidence score 216 may be displayed to the patient using a display device, wherein the display device may be a remote device as discussed previously in this disclosure. Without limitation, confidence score 216 may be an additional output of the model in question, such as, hypertension classifier model 204*a*, hypertension prediction model 204*b*, and/or hypertension correlation model 204*c*. Without limitation, confidence score 216 may be evaluated based on a distance of the output from a given category of output, wherein the distance may be based on a degree to which the model converged during training, and the like. In an embodiment, the output may be represented using vectors, matrices, graphs, and any other data structure described herein. In one or more embodiment, confidence score 216 may be determined using outputs of other models, for example, in certain cases, outputs from different models might agree with the output of the model in question to a greater or lesser extent. In a non-limiting example, level of agreement among outputs may be determined by observing the degree of overlap between fuzzy sets, such as those described below in reference to FIG. 6. Continuing the non-limiting example, the shaded area 632 of FIG. 6 illustrates the aforementioned degree of overlap between fuzzy sets, where the more overlap there is between fuzzy sets, the greater the level of agreement among outputs, and the less overlap there is between fuzzy sets, the lesser the level of agreement among outputs. In an embodiment, the level of agreement among outputs may be produced by another model, wherein the other model's function is to generate confidence scores for each model output based on comparisons with other model outputs.

Figure 2B:
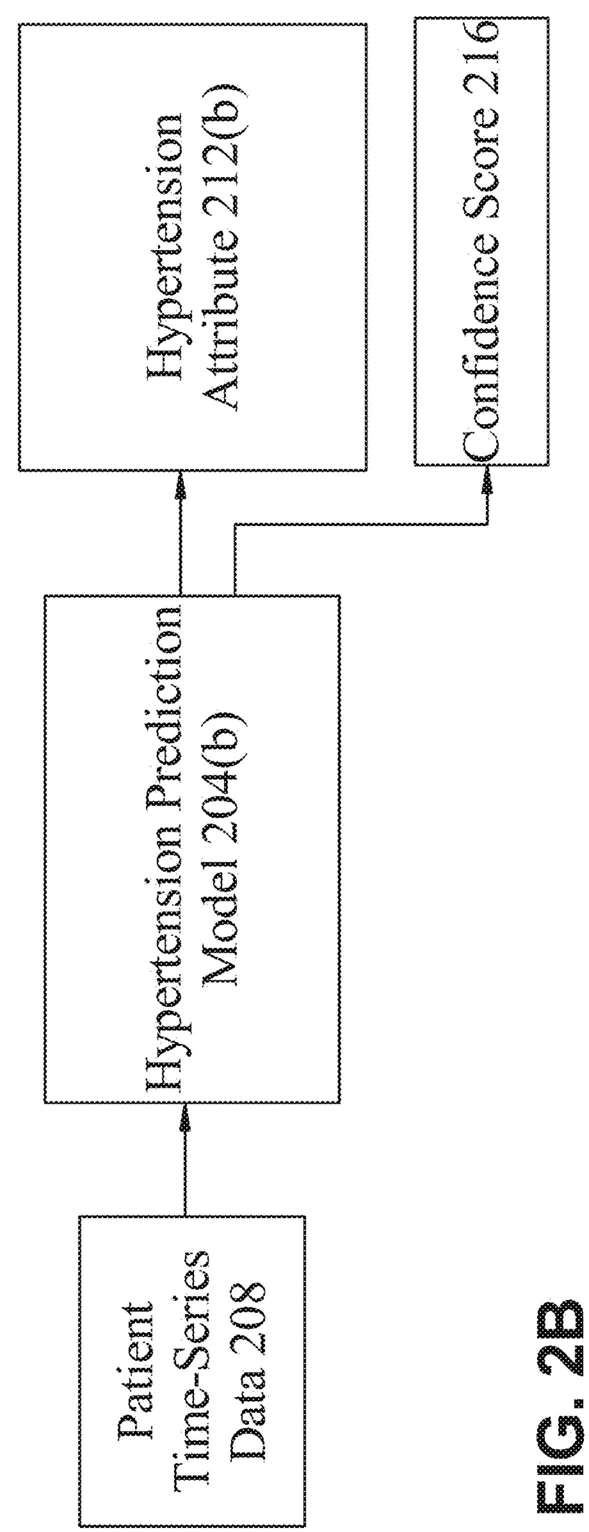
FIG. 2B is an exemplary embodiment of a system for instantiating a hypertension prediction model in accordance with the subject disclosure.

FIG. 2B is an exemplary embodiment of a system, 200*b*, for instantiating a hypertension prediction model in accordance with the subject disclosure. In one or more embodiments, system 200*b* may include hypertension prediction model, 204*b*. In one or more embodiments, hypertension prediction model 204*b* may be trained using patient time-series data 208. In one or more embodiments, hypertension prediction model 204*b* may output hypertension attribute 212*b* and confidence score 216. In one or more embodiments, hypertension prediction model 204*b* may provide a prediction of the patients current blood pressure based on a tolerance of the output (e.g., hypertension attribute 212*b*) accuracy. In one or more embodiments, the tolerance threshold of the output from hypertension prediction model 204*b* may be based on the device used to capture the patient time-series data 208, as well as other parameters and/or assumptions of the hypertension prediction model 204*b*. In one or more embodiments, hypertension prediction model 204*b* may provide the patient with a prediction of patient's future blood pressure level in a specified amount of time. For example, without limitation, hypertension prediction model 204*b* may provide a prediction of patient's blood pressure levels 5 years from the current date based on a plurality of factors including, but not limited to, the patient's age, sex, diet, exercise routines, and the like. In one or more embodiments, confidence score 216 may include an evaluation of the certainty of the hypertension attribute 212*b* based on various parameters. In one or more embodiments, confidence score 216 may include a rating of certainty on a scale of 1 through 5, where 1 is confident and 5 is not confident at all. In one or more embodiments, hypertension attribute 212*b* and/or confidence score 216 may be displayed to the patient using a display device, wherein the display device may be a remote device as discussed previously in this disclosure.

Figure 2C:
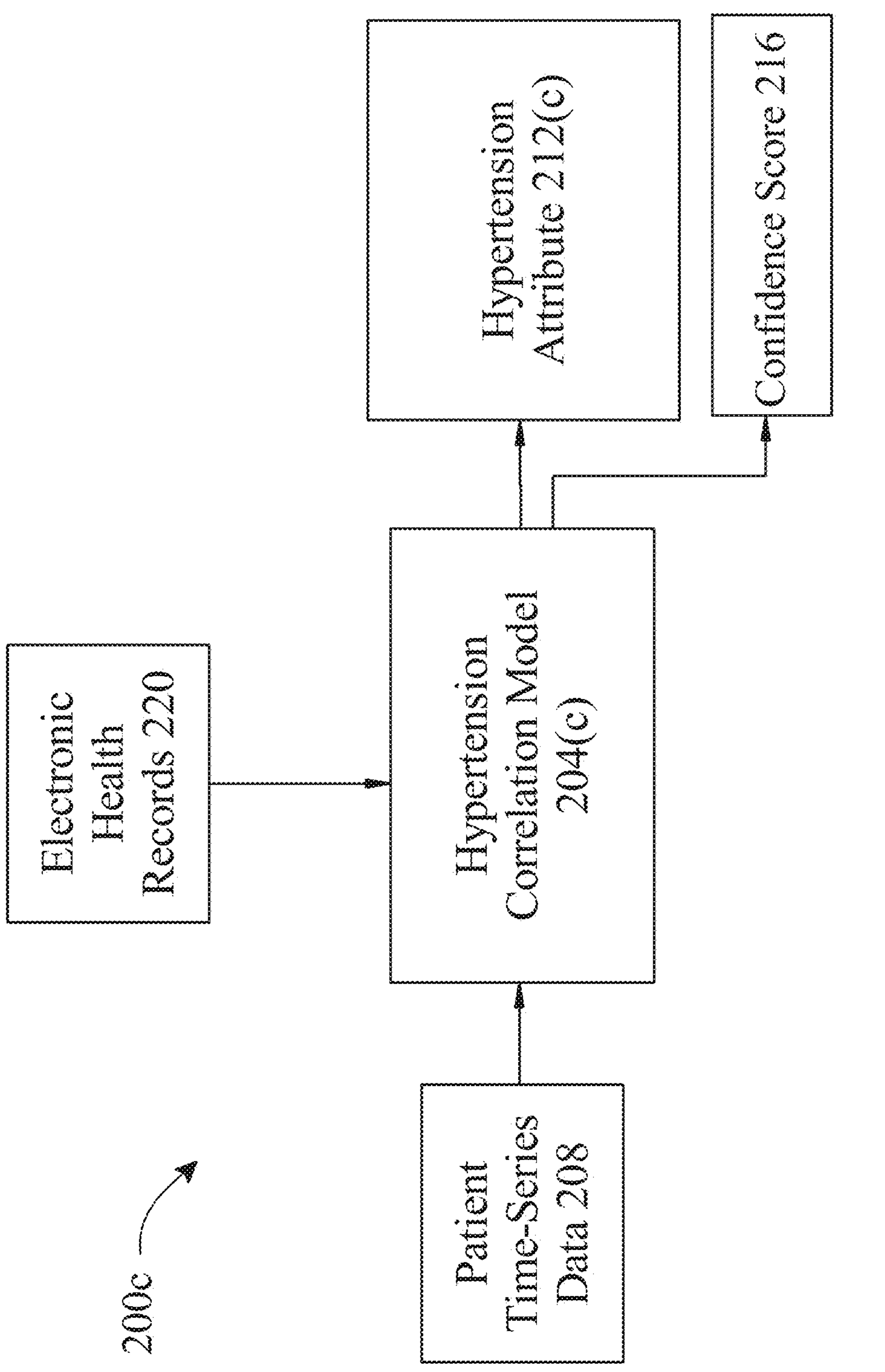
FIG. 2C is an exemplary embodiment of a system for instantiating a hypertension correlation model in accordance with the subject disclosure.

FIG. 2C is an exemplary embodiment of a system, 200*c*, for instantiating a hypertension correlation model in accordance with the subject disclosure. In one or more embodiments, system 200*c* may include hypertension correlation model, 204*c*. In a non-limiting example, hypertension correlation model 204*c* may be the same or substantially the same as the system described in U.S. patent application Ser. No. 18/652,921, filed on May 2, 2024, titled "APPARATUS AND METHOD FOR CLASSIFYING A USER TO A COHORT OF RETROSPECTIVE USERS", which is incorporated by reference herein in its entirety. In one or more embodiments, hypertension correlation model 204*c* may be trained using electronic health records 220. In one or more embodiments, hypertension correlation model 204*c* may receive patient time-series data 208 as input. In one or more embodiments, hypertension correlation model 204*c* may generate hypertension attribute 212*c* and confidence score 216 as outputs. In one or more embodiments, electronic health records 220 may include a plurality of ECG signal data and/or ECG electronic image data. In one or more embodiments, hypertension correlation model 204*c* may analyze electronic health records 220, segment portions of the ECG signal data to define a particular signal characteristic, generate a label for the segmented portion of the ECG signal data, and generate hypertension attribute 212*c*. In one or more embodiments, confidence score 220 may include a rating of certainty on a scale of 1 through 5, where 1 is confident and 5 is not confident at all. In one or more embodiments, hypertension attribute 212*b* and/or confidence score 216 may be displayed to the patient using a display device, wherein the display device may be a remote device as discussed previously in this disclosure.

Referring now to FIG. 3, an exemplary embodiment of a machine-learning module 300 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 304 to generate an algorithm instantiated in hardware or software logic, data structures, and/or functions that will be performed by a computing device/module to produce outputs 308 given data provided as inputs 312; this is in contrast to a non-machine learning software program where the commands to be executed are determined in advance by a user and written in a programming language.

Still referring to FIG. 3, "training data," as used herein, is data containing correlations that a machine-learning process may use to model relationships between two or more categories of data elements. For instance, and without limitation, training data 304 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 304 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 304 according to various correlations; correlations may indicate causative and/or predictive links between categories of data elements, which may be modeled as relationships such as mathematical relationships by machine-learning processes as described in further detail below. Training data 304 may be formatted and/or organized by categories of data elements, for instance by associating data elements with one or more descriptors corresponding to categories of data elements. As a non-limiting example, training data 304 may include data entered in standardized forms by persons or processes, such that entry of a given data element in a given field in a form may be mapped to one or more descriptors of categories. Elements in training data 304 may be linked to descriptors of categories by tags, tokens, or other data elements; for instance, and without limitation, training data 304 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 3, training data 304 may include one or more elements that are not categorized; that is, training data 304 may not be formatted or contain descriptors for some elements of data. Machine-learning algorithms and/or other processes may sort training data 304 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 304 to be made applicable for two or more distinct machine-learning algorithms as described in further detail below. Training data 304 used by machine-learning module 300 may correlate any input data as described in this disclosure to any output data as described in this disclosure. As a non-limiting illustrative example patient time-series data (e.g., patient electrocardiogram signals) may be input into machine-learning module 300 and machine-learning module 300 may output a hypertension attribute and/or a confidence score.

Further referring to FIG. 3, training data may be filtered, sorted, and/or selected using one or more supervised and/or unsupervised machine-learning processes and/or models as described in further detail below; such models may include without limitation a training data classifier 316. Training data classifier 316 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 300 may generate a classifier using a classification algorithm, defined as a processes whereby a computing device and/or any module and/or component operating thereon derives a classifier from training data 304. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 316 may classify elements of training data to specific signal characteristics, such as, without limitation, signal characteristics related to hypertension.

Still referring to FIG. 3, Computing device may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as P(A/B)=P(B/A) P(A)=P(B), where P(A/B) is the probability of hypothesis A given data B also known as posterior probability; P(B/A) is the probability of data B given that the hypothesis A was true; P(A) is the probability of hypothesis A being true regardless of data also known as prior probability of A; and P(B) is the probability of the data regardless of the hypothesis. A naïve Bayes algorithm may be generated by first transforming training data into a frequency table. Computing device may then calculate a likelihood table by calculating probabilities of different data entries and classification labels. Computing device may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 3, Computing device may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 3, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below.

Any vectors as described herein may be scaled, such that each vector represents each attribute along an equivalent scale of values. Each vector may be "normalized," or divided by a "length" attribute, such as a length attribute/as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 3, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 3, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 3, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 3, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 3, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 3, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 3, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 3, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation σ of a set or subset of values:

$$X_{new} = \frac{X - X_{mean}}{\sigma}.$$

Scaling may be performed using a median value of a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 3, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, and generation of modified copies of existing entries and/or examples. Augmentation may include performing one or more transformations on data, such as geometric, color space, affine, brightness, cropping, and/or contrast transformations of images.

Still referring to FIG. 3, machine-learning module 300 may be configured to perform a lazy-learning process 320 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 304. Heuristic may include selecting some number of highest-ranking associations and/or training data 304 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 3, machine-learning processes as described in this disclosure may be used to generate machine-learning models 324. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 324 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 324 may be generated by creating an artificial neural network, such as a convolutional neural network comprising an input layer of nodes, one or more intermediate layers, and an output layer of nodes. Connections between nodes may be created via the process of "training" the network, in which elements from a training data 304 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 3, machine-learning algorithms may include at least a supervised machine-learning process 328. At least a supervised machine-learning process 328, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described in this disclosure, as inputs, and outputs, as described in this disclosure, as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 304. Persons skilled in the art, upon reviewing the entirety of this disclosure, will be aware of various possible variations of at least a supervised machine-learning process 328 that may be used to determine relation between inputs and outputs. Supervised machine-learning processes may include classification algorithms as defined above.

With further reference to FIG. 3, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 3, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 3, machine learning processes may include at least an unsupervised machine-learning processes 332. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 332 may not require a response variable; unsupervised processes 332 may be used to find interesting patterns and/or inferences between variables, to determine a degree of correlation between two or more variables, or the like.

Still referring to FIG. 3, machine-learning module 300 may be designed and configured to create a machine-learning model 324 using techniques for development of linear regression models. Linear regression models may include ordinary least squares regression, which aims to minimize the square of the difference between predicted outcomes and actual outcomes according to an appropriate norm for measuring such a difference (e.g., a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the clastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g., a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 3, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 3, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 3, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 3, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as “desired” results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 3, one or more processes or algorithms described above may be performed by at least a dedicated hardware unit 336. A “dedicated hardware unit,” for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 336 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 336 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 336 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 4:
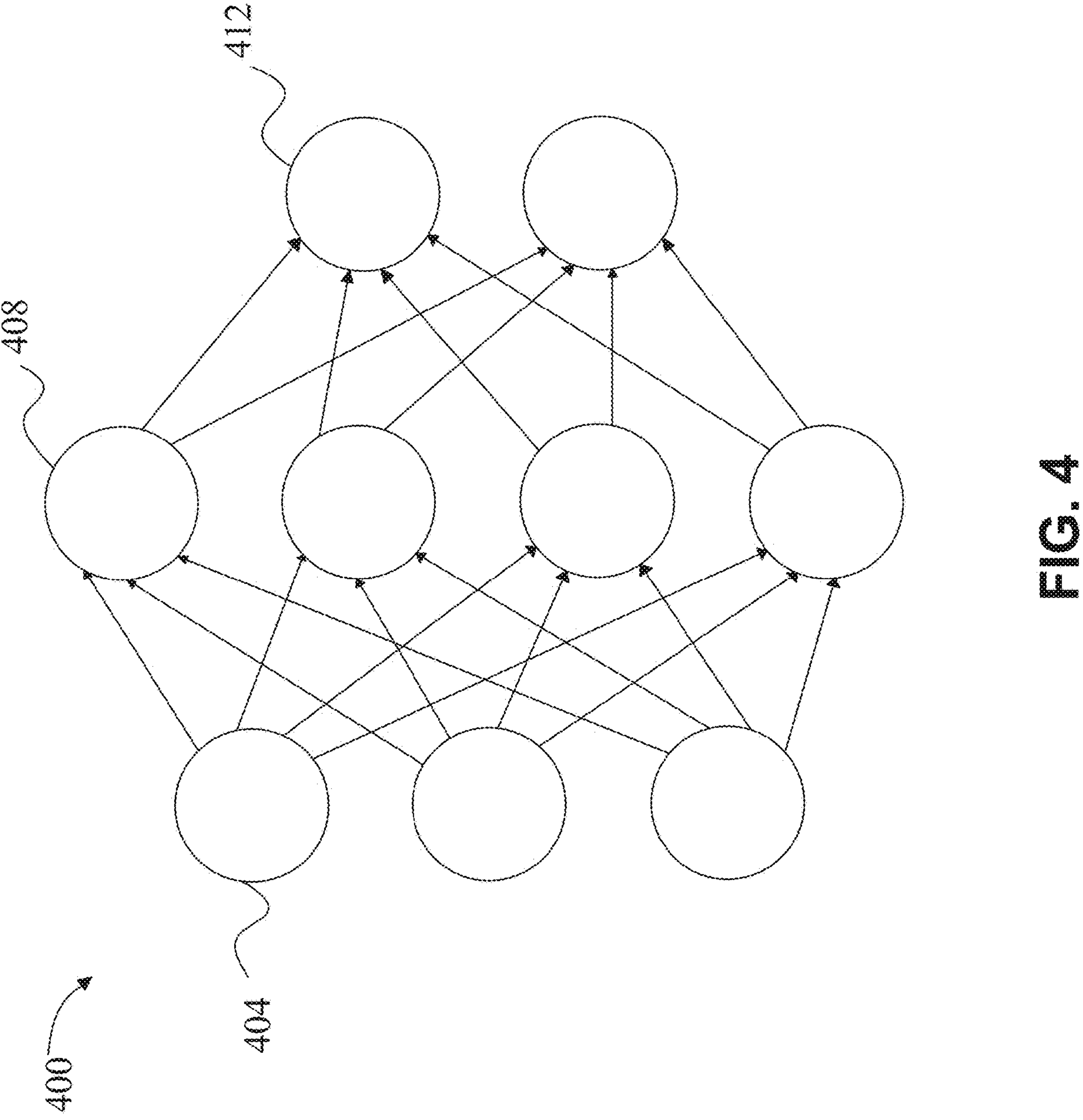
FIG. 4 is a diagram of an exemplary embodiment of a neural network.

Referring now to FIG. 4, an exemplary embodiment of neural network 400 is illustrated. A neural network 400 also known as an artificial neural network, is a network of “nodes,” or data structures having one or more inputs, one or more outputs, and a function determining outputs based on inputs. Such nodes may be organized in a network, such as without limitation a convolutional neural network, including an input layer of nodes 404, one or more intermediate layers 408, and an output layer of nodes 412. Connections between nodes may be created via the process of “training” the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a “feed-forward” network, or may feed outputs of one layer back to inputs of the same or a different layer in a “recurrent network.” As a further non-limiting example, a neural network may include a convolutional neural network comprising an input layer of nodes, one or more intermediate layers, and an output layer of nodes. A “convolutional neural network,” as used in this disclosure, is a neural network in which at least one hidden layer is a convolutional layer that convolves inputs to that layer with a subset of inputs known as a “kernel,” along with one or more additional layers such as pooling layers, fully connected layers, and the like.

Figure 5:
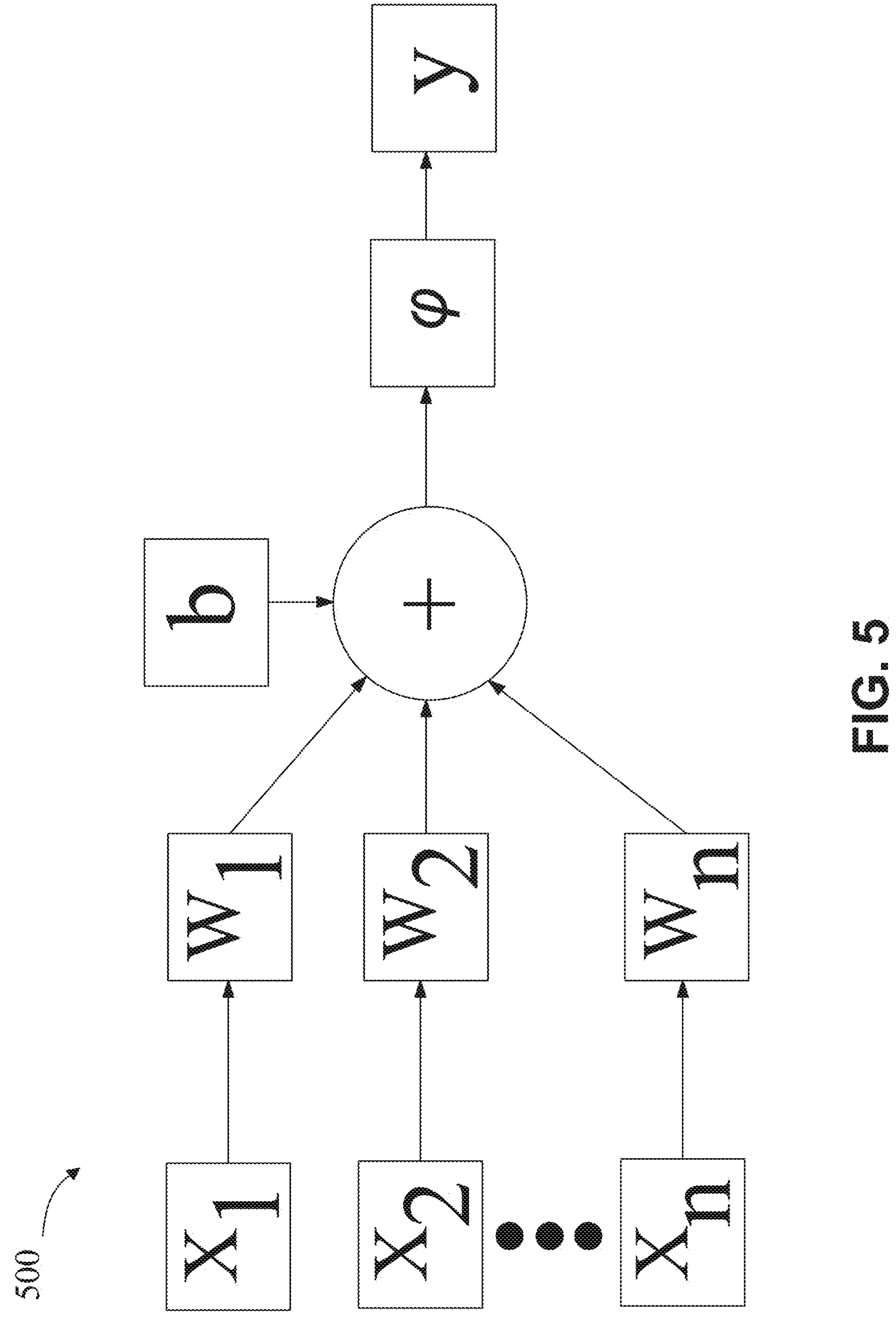
FIG. 5 is a diagram of an exemplary embodiment of a node of a neural network.

Referring now to FIG. 5, an exemplary embodiment of a node 500 of a neural network is illustrated. A node may include, without limitation, a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as $f(x)=\tanh^2(x)$, a rectified linear unit function such as $f(x)=\max(0, x)$, a “leaky” and/or "parametric" rectified linear unit function such as $f(x)=\max(ax, x)$ for some a, an exponential linear units function such as $$f(x)=\begin{cases} x \text{ for } x \geq 0 \\ \alpha(e^x-1) \text{ for } x < 0 \end{cases}$$

for some value of α (this function may be replaced and/or weighted by its own derivative in some embodiments), a softmax function such as $$f(x_i)=\frac{e^x}{\sum_i x_i}$$

where the inputs to an instant layer are $x_i$, a swish function such as $f(x)=x*\text{sigmoid}(x)$, a Gaussian error linear unit function such as $f(x)=a(1+\tanh(\sqrt{2/\pi}(x+bx^r)))$ for some values of a, b, and r, and/or a scaled exponential linear unit function such as $$f(x)=\lambda\begin{cases} \alpha(e^x-1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function σ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Referring to FIG. 6, an exemplary embodiment of fuzzy set comparison 600 is illustrated. A first fuzzy set 604 may be represented, without limitation, according to a first membership function 608 representing a probability that an input falling on a first range of values 612 is a member of the first fuzzy set 604, where the first membership function 608 has values on a range of probabilities such as without limitation the interval [0,1], and an area beneath the first membership function 608 may represent a set of values within first fuzzy set 604. Although first range of values 612 is illustrated for clarity in this exemplary depiction as a range on a single number line or axis, first range of values 612 may be defined on two or more dimensions, representing, for instance, a Cartesian product between a plurality of ranges, curves, axes, spaces, dimensions, or the like. First membership function 608 may include any suitable function mapping first range 612 to a probability interval, including without limitation a triangular function defined by two linear elements such as line segments or planes that intersect at or below the top of the probability interval. As a non-limiting example, triangular membership function may be defined as:

$$y(x, a, b, c)=\begin{cases} 0, \text{ for } x > c \text{ and } x < a \\ \frac{x-a}{b-a}, \text{ for } a \leq x < b \\ \frac{c-x}{c-b}, \text{ if } b < x \leq c \end{cases}$$

a trapezoidal membership function may be defined as:

$$y(x, a, b, c, d)=\max\left(\min\left(\frac{x-a}{b-a}, 1, \frac{d-x}{d-c}\right), 0\right)$$

a sigmoidal function may be defined as:

$$y(x, a, c)=\frac{1}{1-e^{-a(x-c)}}$$

a Gaussian membership function may be defined as:

$$y(x, c, \sigma)=e^{-\frac{1}{2}\left(\frac{x-c}{\sigma}\right)^2}$$

and a bell membership function may be defined as:

$$y(x, a, b, c,)=\left[1+\left|\frac{x-c}{a}\right|^{2b}\right]^{-1}$$

Persons skilled in the art, upon reviewing the entirety of this disclosure, will be aware of various alternative or additional membership functions that may be used consistently with this disclosure.

Still referring to FIG. 6, first fuzzy set 604 may represent any value or combination of values as described above, including output from one or more machine-learning models, patient time-series data, and a predetermined class, such as without limitation of signal characteristics. A second fuzzy set 616, which may represent any value which may be represented by first fuzzy set 604, may be defined by a second membership function 620 on a second range 624; second range 624 may be identical and/or overlap with first range 612 and/or may be combined with first range via Cartesian product or the like to generate a mapping permitting evaluation overlap of first fuzzy set 604 and second fuzzy set 616. Where first fuzzy set 604 and second fuzzy set 616 have a region 628 that overlaps, first membership function 608 and second membership function 620 may intersect at a point 632 representing a probability, as defined on probability interval, of a match between first fuzzy set 604 and second fuzzy set 616. Alternatively or additionally, a single value of first and/or second fuzzy set may be located at a locus 636 on first range 612 and/or second range 624, where a probability of membership may be taken by evaluation of first membership function 608 and/or second membership function 620 at that range point. A probability at 628 and/or 632 may be compared to a threshold 640 to determine whether a positive match is indicated. Threshold 640 may, in a non-limiting example, represent a degree of match between first fuzzy set 604 and second fuzzy set 616, and/or single values therein with each other or with either set, which is sufficient for purposes of the matching process; for instance, threshold may indicate a sufficient degree of overlap between an output from one or more machine-learning models and/or patient time-series data and a predetermined class, such as without limitation signal characteristics categorization, for combination to occur as described above. Alternatively or additionally, each threshold may be tuned by a machine-learning and/or statistical process, for instance and without limitation as described in further detail below.

Further referring to FIG. 6, in an embodiment, a degree of match between fuzzy sets may be used to classify a patient time-series data with signal characteristics. For instance, if a signal characteristics has a fuzzy set matching patient time-series data fuzzy set by having a degree of overlap exceeding a threshold, computing device may classify the patient time-series data as belonging to the signal characteristics categorization. Where multiple fuzzy matches are performed, degrees of match for each respective fuzzy set may be computed and aggregated through, for instance, addition, averaging, or the like, to determine an overall degree of match.

Still referring to FIG. 6, in an embodiment, a patient time-series data may be compared to multiple signal characteristics categorization fuzzy sets. For instance, patient time-series data may be represented by a fuzzy set that is compared to each of the multiple signal characteristics categorization fuzzy sets; and a degree of overlap exceeding a threshold between the patient time-series data fuzzy set and any of the multiple signal characteristics categorization fuzzy sets may cause computing device to classify the patient time-series data as belonging to signal characteristics categorization. For instance, in one embodiment there may be two signal characteristics categorization fuzzy sets, representing respectively first signal characteristic categorization and a second signal characteristic categorization. First signal characteristics categorization may have a first fuzzy set; Second signal characteristics categorization may have a second fuzzy set; and patient time-series data may have a patient time-series data fuzzy set. Computing device, for example, may compare a patient time-series data fuzzy set with each of signal characteristics categorization fuzzy set and signal characteristics categorization fuzzy set, as described above, and classify a patient time-series data to either, both, or neither of signal characteristics categorization nor signal characteristics categorization. Machine-learning methods as described throughout may, in a non-limiting example, generate coefficients used in fuzzy set equations as described above, such as without limitation x, c, and σ of a Gaussian set as described above, as outputs of machine-learning methods. Likewise, patient time-series data may be used indirectly to determine a fuzzy set, as patient time-series data fuzzy set may be derived from outputs of one or more machine-learning models that take the patient time-series data directly or indirectly as inputs.

Still referring to FIG. 6, a computing device may use a logic comparison program, such as, but not limited to, a fuzzy logic model to determine a signal characteristics response. An signal characteristics response may include, but is not limited to, elevated blood pressure, hypertension stage 1, hypertension stage 2, hypertensive crisis, and the like; each such signal characteristics response may be represented as a value for a linguistic variable representing signal characteristics response or in other words a fuzzy set as described above that corresponds to a degree of similarity as calculated using any statistical, machine-learning, or other method that may occur to a person skilled in the art upon reviewing the entirety of this disclosure. In other words, a given element of patient time-series data may have a first non-zero value for membership in a first linguistic variable value such as "elevated blood pressure" and a second non-zero value for membership in a second linguistic variable value such as "stage 1 hypertension." In some embodiments, determining a signal characteristics categorization may include using a linear regression model. A linear regression model may include a machine learning model. A linear regression model may be configured to map data of patient time-series data, such as degree of similarity to one or more signal characteristics parameters from electronic health records. A linear regression model may be trained using a machine learning process. A linear regression model may map statistics such as, but not limited to, quality of patient time-series data. In some embodiments, determining a signal characteristics of patient time-series data may include using a signal characteristics classification model. A signal characteristics classification model may be configured to input collected data and cluster data to a centroid based on, but not limited to, frequency of appearance, linguistic indicators of quality, and the like. Centroids may include scores assigned to them such that quality of similarity of patient time-series data may each be assigned a score. In some embodiments signal characteristics classification model may include a K-means clustering model. In some embodiments, signal characteristics classification model may include a particle swarm optimization model. In some embodiments, determining the signal characteristics of a patient time-series data may include using a fuzzy inference engine. A fuzzy inference engine may be configured to map one or more patient time-series data elements using fuzzy logic. In some embodiments, patient time-series data may be arranged by a logic comparison program into signal characteristics arrangement. An "signal characteristics arrangement" as used in this disclosure is any grouping of objects and/or data based on skill level and/or output score. This step may be implemented as described above in FIGS. 1-5. Membership function coefficients and/or constants as described above may be tuned according to classification and/or clustering algorithms. For instance, and without limitation, a clustering algorithm may determine a Gaussian or other distribution of questions about a centroid corresponding to a given hypertension level, and an iterative or other method may be used to find a membership function, for any membership function type as described above, that minimizes an average error from the statistically determined distribution, such that, for instance, a triangular or Gaussian membership function about a centroid representing a center of the distribution that most closely matches the distribution. Error functions to be minimized, and/or methods of minimization, may be performed without limitation according to any error function and/or error function minimization process and/or method as described in this disclosure.

Figure 7:
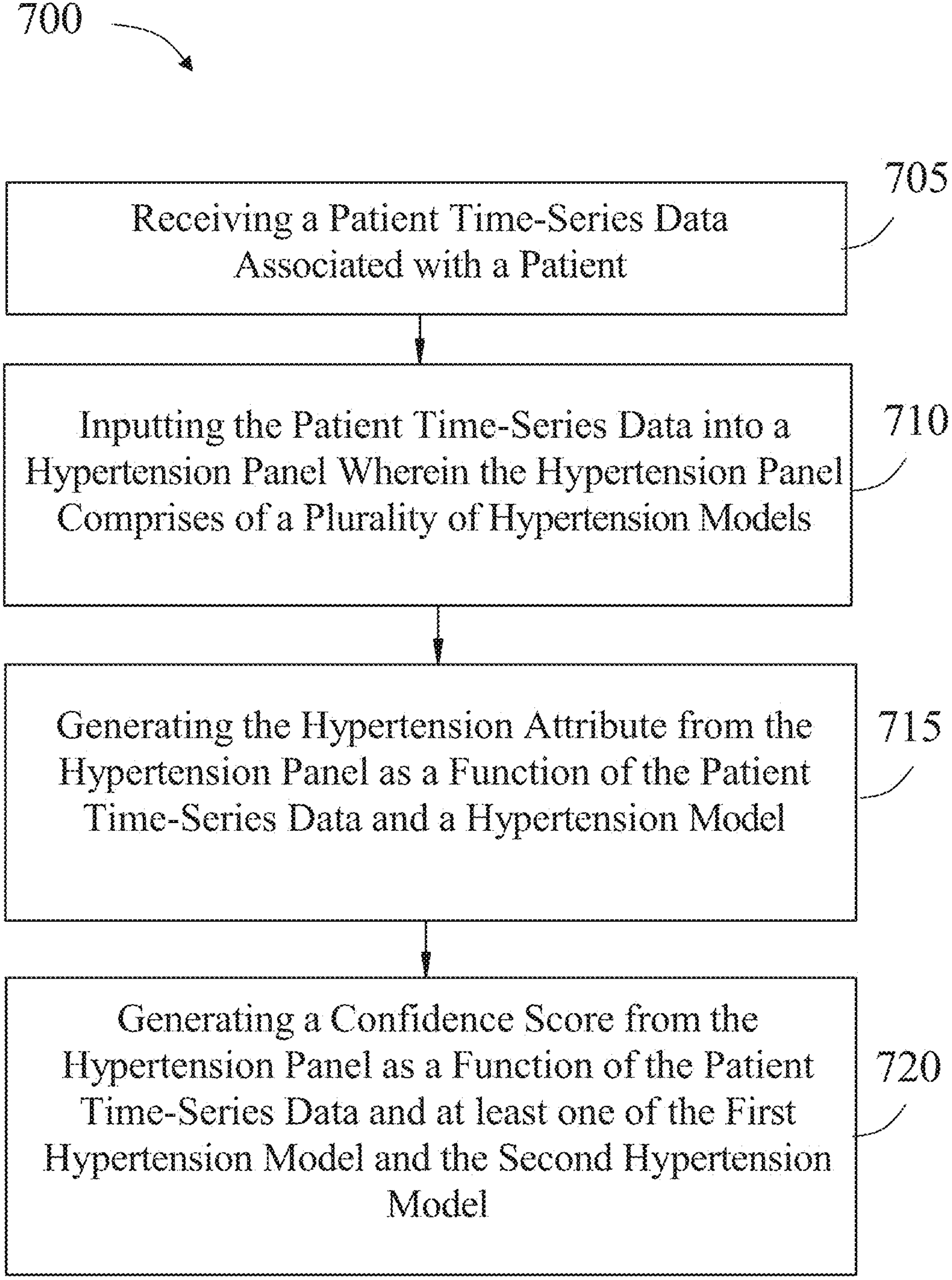
FIG. 7 is a block diagram of an exemplary method for detecting hypertension attributes in a patient time-series data.

Referring now to FIG. 7, a flow diagram of an exemplary method 700 detecting hypertension attributes in a patient time-series data is illustrated. At step 705, method 700 includes receiving, using at least a processor, a patient time-series data associated with a patient, wherein the patient time-series data is captured using a measurement device. This may be implemented as described and with reference to FIGS. 1-6.

Still referring to FIG. 7, at step 710, method 700 includes inputting, using at least a processor, the patient time-series data into a hypertension panel wherein the hypertension panel may include of a plurality of hypertension models. In an embodiment, the hypertension model may include a matrix. In another non-limiting embodiment, the hypertension panel is configured to receive the patient time-series data as an input, calculate the hypertension attribute, and output the hypertension attribute. In another embodiment, the plurality of hypertension models comprise a hypertension classifier model, a hypertension prediction model, and a hypertension correlation model. In another embodiment, training the hypertension model may include receiving a plurality of a patient time-series data associated with a plurality of patients, pretraining hypertension model in the hypertension panel as a function of the plurality of patient time-series data examples by adjusting one or more parameter attributes of the hypertension model, and training the hypertension model as a function of the parameter attributes and an electronic health records. In an embodiment, inputting the patient time-series data into the hypertension panel may include selecting the hypertension model from a plurality of hypertension models as a function of a patient input and the graphical user interface. This may be implemented as described and with reference to FIGS. 1-6.

Still referring to FIG. 7, at step 715, method 700 includes generating, using at least a processor, the hypertension attribute from the hypertension panel as a function of the patient time-series data and a hypertension model, wherein the hypertension attribute may include generating, using a first hypertension model, a first hypertension attribute comprising a measurement of the patient yielding a first hypertension level, generating, using a second hypertension model, a second hypertension attribute comprising a measurement of the patient yielding a second hypertension level, and generating the hypertension attribute using the patient time-series data and at least one of the first hypertension model and the second hypertension model. In another non-limiting embodiment, the hypertension level may include a systolic blood pressure and a diastolic blood pressure. In an embodiment, the hypertension attribute may include a hypertension deviation, wherein the hypertension deviation may include a change in the hypertension attribute. This may be implemented as described and with reference to FIGS. 1-6.

Still referring to FIG. 7, at step 720, method 700 includes generating, using at least a processor, a confidence score from the hypertension panel as a function of the patient time-series data and at least one of the first hypertension model and the second hypertension model. This may be implemented as described and with reference to FIGS. 1-6.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
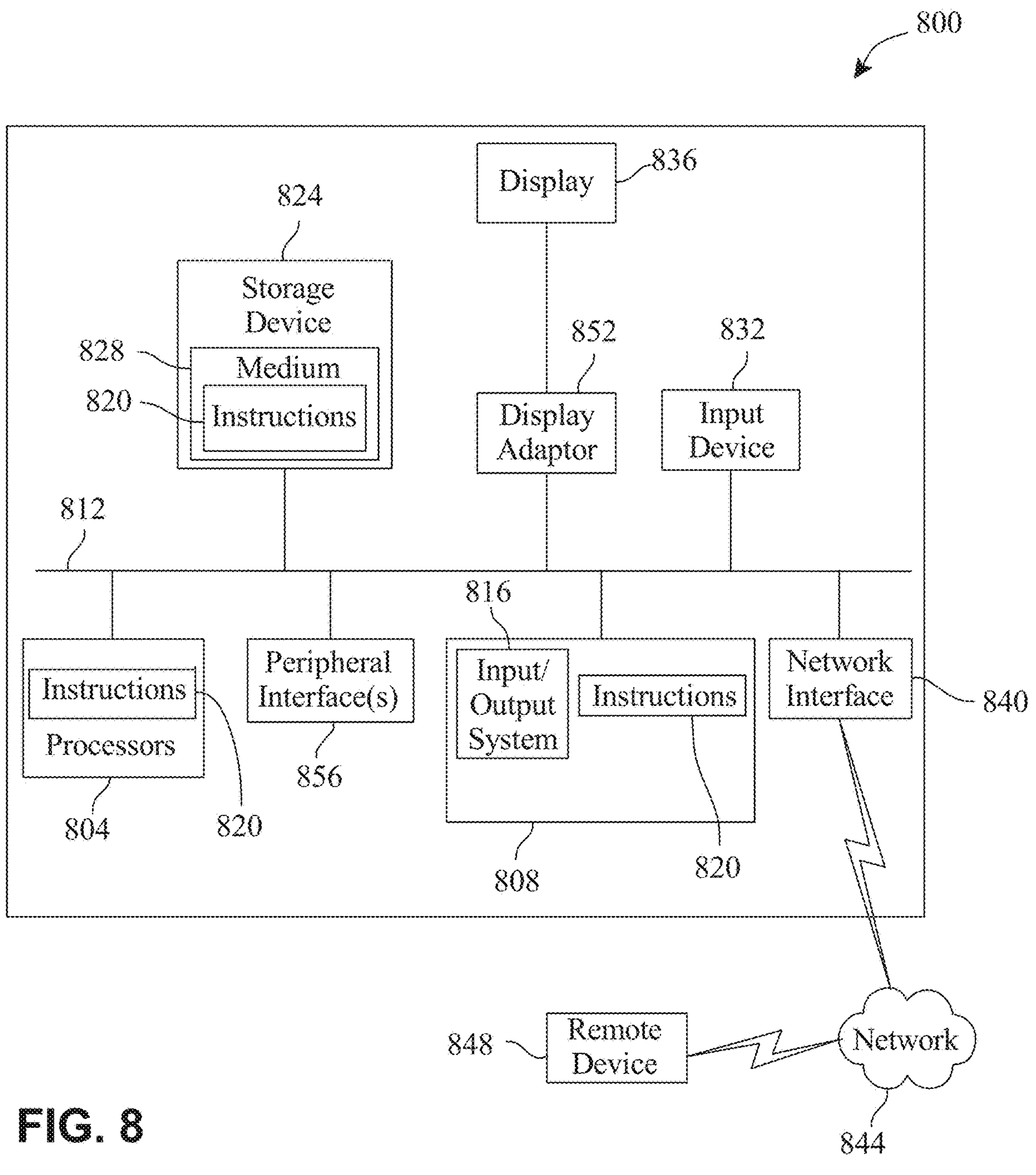
FIG. 8 is a block diagram of a computing system that can be used to implement any one or more of the methodologies disclosed herein and any one or more portions thereof.

FIG. 8 shows a diagrammatic representation of one embodiment of computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 924 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIREWIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed:

1. An apparatus for detecting hypertension attributes in a patient time-series data, the apparatus comprising:
- at least a processor; and
- a memory communicatively connected to the at least a processor, wherein the memory contains instructions configuring the at least a processor to:
  - receive a patient time-series data associated with a patient, wherein the patient time-series data is captured using a measurement device, communicatively connected to the at least a processor, comprising at least a transducer wherein the transducer operates as a low-pass filter, responding to input stimuli with a delay and filtering signals above a maximum detectable frequency determined by the transducer's response time;

generate one or more vectors from the patient time-series data, wherein each vector represents quantitative values associated with hypertension attributes, map the one or more vectors into a vector space, and organize the one or more vectors into a matrix used by a plurality of hypertension models;

input the matrix of patient time-series data into a hypertension panel, wherein the hypertension panel comprises the plurality of hypertension models further comprising at least a first hypertension model and a second hypertension model; and generate a hypertension attribute from the hypertension panel as a function of the patient time-series data and the hypertension panel, wherein the hypertension attribute comprises a probability of the patient developing a future heart condition, wherein generating the hypertension attribute comprises:

generating training data for the plurality of hypertension models in the hypertension panel based on previous iterations of receiving patient time-series data using the measurement device;

training the first hypertension model and the second hypertension model with the training data;

generating, using the first hypertension model, a first hypertension attribute comprising a measurement of the patient yielding a first hypertension level using the patient time-series data; and generating, using the second hypertension model, a second hypertension attribute using the patient time-series data.

2. The apparatus of claim 1, wherein the instructions further configure the at least a processor to generate a confidence score from the hypertension panel as a function of the patient time-series data and at least one of the first hypertension model and the second hypertension model.

3. The apparatus of claim 1, wherein the first hypertension level comprises a systolic blood pressure and a diastolic blood pressure.

4. The apparatus of claim 1, wherein the second hypertension model comprises one or more of a hypertension classifier model, a hypertension prediction model, and a hypertension correlation model.

5. The apparatus of claim 1, wherein the second hypertension model comprises a loss function.

6. The apparatus of claim 1, wherein training the second hypertension model comprises:

adjusting one or more parameter attributes of the first hypertension model; and training the second hypertension model as a function of the parameter attributes and an electronic health record.

7. The apparatus of claim 1, wherein the hypertension attribute comprises a hypertension deviation, wherein the hypertension deviation comprises a change in the hypertension attribute.

8. The apparatus of claim 1, wherein inputting the patient time-series data into the hypertension panel comprises selecting the second hypertension model from a plurality of hypertension models as a function of an input and a graphical user interface.

9. The apparatus of claim 1, further comprising displaying the hypertension attribute by:

comparing the hypertension attribute to a target blood pressure level; and displaying the hypertension attribute as a function of the comparison.

10. The apparatus of claim 9, further comprising displaying the hypertension attribute through a graphical user interface by generating a visual element associated with the hypertension attribute, wherein the visual element is further associated with an event handler.

11. A method for detecting hypertension attributes in a patient time-series data, the method comprising:

receiving a patient time-series data associated with a patient, wherein the patient time-series data is captured using a measurement device, communicatively connected to the at least a processor, comprising at least a transducer wherein the transducer operates as a low-pass filter, responding to input stimuli with a delay and filtering signals above a maximum detectable frequency determined by the transducer's response time;

generating one or more vectors from the patient time-series data, wherein each vector represents quantitative values associated with hypertension attributes, mapping the one or more vectors into a vector space, and organizing the one or more vectors into a matrix used by a plurality of hypertension models;

inputting the matrix of patient time-series data into a hypertension panel, wherein the hypertension panel comprises the plurality of hypertension models further comprising at least a first hypertension model and a second hypertension model; and generating a hypertension attribute from the hypertension panel as a function of the patient time-series data and the hypertension panel, wherein the hypertension attribute comprises a probability of the patient developing a future heart condition, wherein generating the hypertension attribute comprises:

generating training data for the plurality of hypertension models in the hypertension panel based on previous iterations of receiving patient time-series data using the measurement device;

training the first hypertension model and the second hypertension model with the training data;

generating, using the first hypertension model, a first hypertension attribute comprising a measurement of the patient yielding a first hypertension level using the patient time-series data; and generating, using the second hypertension model, a second hypertension attribute using the patient time-series data.

12. The method of claim 11, further comprising generating a confidence score from the hypertension panel as a function of the patient time-series data and at least one of the first hypertension model and the second hypertension model.

13. The method of claim 11, wherein the first hypertension level comprises a systolic blood pressure and a diastolic blood pressure.

14. The method of claim 11, wherein the second hypertension model comprises one or more of a hypertension classifier model, a hypertension prediction model, and a hypertension correlation model.

15. The method of claim 11, wherein the second hypertension model comprises a loss function.

16. The method of claim 11, wherein training the second hypertension model comprises:

adjusting one or more parameter attributes of the first hypertension model; and training the second hypertension model as a function of the parameter attributes and an electronic health record.

17. The method of claim 11, wherein the hypertension attribute comprises a hypertension deviation, wherein the hypertension deviation comprises a change in the hypertension attribute.

18. The method of claim 11, wherein inputting the patient time-series data into the hypertension panel comprises selecting the second hypertension model from a plurality of hypertension models as a function of an input and a graphical user interface.

19. The method of claim 11, further comprising displaying the hypertension attribute by:

comparing the hypertension attribute to a target blood pressure level; and displaying the hypertension attribute as a function of the comparison.

20. The method of claim 19, further comprising displaying the hypertension attribute through a graphical user interface by generating a visual element associated with the hypertension attribute, wherein the visual element is further associated with an event handler.

* * * * *